(12) United States Patent
Diallo et al.

(10) Patent No.: US 12,076,353 B2
(45) Date of Patent: Sep. 3, 2024

(54) COMPOSITIONS AND METHODS FOR ENHANCING PRODUCTION, GROWTH, SPREAD, OR ONCOLYTIC AND IMMUNOTHERAPEUTIC EFFICACY OF INTERFERON-SENSITIVE VIRUSES

(71) Applicant: Ottawa Hospital Research Institute, Ottawa (CA)

(72) Inventors: Jean-Simon Diallo, Ottawa (CA); Mohammed Selman, Ann Arbor, MI (US); Rozanne Arulanandam, Orleans (CA); Nicole Elise Forbes, Ottawa (CA); Ramya Krishnan, Hamilton (CA)

(73) Assignee: OTTAWA HOSPITAL RESEARCH INSTITUTE, Ottawa (CA)

( * ) Notice: Subject to any disclaimer, the term of this patent is extended or adjusted under 35 U.S.C. 154(b) by 765 days.

(21) Appl. No.: 16/763,013

(22) PCT Filed: Nov. 23, 2018

(86) PCT No.: PCT/CA2018/051492
§ 371 (c)(1),
(2) Date: May 11, 2020

(87) PCT Pub. No.: WO2019/100163
PCT Pub. Date: May 31, 2019

(65) Prior Publication Data
US 2020/0276253 A1  Sep. 3, 2020

Related U.S. Application Data

(60) Provisional application No. 62/590,456, filed on Nov. 24, 2017.

(51) Int. Cl.
| | | |
|---|---|---|
| *C12N 7/00* | (2006.01) |
| *A61K 31/225* | (2006.01) |
| *A61K 35/766* | (2015.01) |
| *A61P 35/00* | (2006.01) |
| *C07C 69/60* | (2006.01) |
| *A61K 39/00* | (2006.01) |

(52) U.S. Cl.
CPC .......... *A61K 35/766* (2013.01); *A61K 31/225* (2013.01); *A61P 35/00* (2018.01); *C07C 69/60* (2013.01); *C12N 7/00* (2013.01); *A61K 2039/585* (2013.01); *C12N 2710/10332* (2013.01); *C12N 2710/10351* (2013.01); *C12N 2740/16134* (2013.01); *C12N 2760/16134* (2013.01); *C12N 2760/16151* (2013.01); *C12N 2760/20232* (2013.01); *C12N 2760/20251* (2013.01)

(58) Field of Classification Search
None
See application file for complete search history.

(56) References Cited

U.S. PATENT DOCUMENTS

2012/0230958 A1  9/2012  Kirn
2015/0133507 A1  5/2015  Kahrs

OTHER PUBLICATIONS

Rodriquez-Spong et al., Advanced Drug Delivery Reviews, 2004, 56: 241-274. (Year: 2004).*
Du Y., et al. Genome-wide identification of interferon-sensitive mutations enables influenza vaccine design. Science. Jan. 19, 2018;359(6373):290-296. doi: 10.1126/science.aan8806. PMID: 29348231. (abstract only).
Le T. H., et al. The State of The Jak/Stat Pathway Affects the Sensitivity of TumorCells to Oncolytic Enteroviruses. Mol Biol (Mosk). Jul.-Aug. 2020;54(4):634-642. Russian. doi: 10.31857/S0026898420040102. PMID: 32799226. (abstract only).
Liikanen I., et al. Induction of interferon pathways mediates in vivo resistance to oncolytic adenovirus. Mol Ther. Oct. 2011;19(10):1858-66. doi: 10.1038/mt.2011.144. Epub Jul. 26, 2011. PMID: 21792178; PMCID: PMC3188743.
Locke M. C., et al. Interferon Alpha, but Not Interferon Beta, Acts Early to Control Chronic Chikungunya Virus Pathogenesis. J Virol. Jan. 12, 2022;96(1):e0114321. doi: 10.1128/JVI.01143-21. Epub Oct. 20, 2021. PMID: 34668781; PMCID: PMC8754211.
Diamond M. S., et al. Interferon inhibits dengue virus infection by preventing translation of viral RNA through a PKR-independent mechanism. Virology. Oct. 25, 2001;289(2):297-311. doi: 10.1006/viro.2001.1114. PMID: 11689052.
Paulmann D., et al. Hepatitis A virus protein 2B suppresses beta interferon (IFN) gene transcription by interfering with IFN regulatory factor 3 activation. J Gen Virol. Jul. 2008;89(Pt 7):1593-1604. doi: 10.1099/vir.0.83521-0. PMID: 18559929.
Shibaki T., et al. Participation of type I interferon in the decreased virulence of the UL13 gene-deleted mutant of herpes simplex virus type 1. J Interferon Cytokine Res. May 2001;21(5):279-85. doi: 10.1089/107999001300177466. PMID: 11429158.
Richman D. D., et al. Three strains of influenza A virus (H3N2): interferon sensitivity in vitro and interferon production In volunteers. J Clin Microbiol. Mar. 1976;3(3):223-6. doi: 10.1128/jcm.3.3.223-226.1976. PMID: 1270590; PMCID: PMC274274.
Djavani M., et al. Role of the promyelocytic leukemia protein PML in the interferon sensitivity of lymphocytic choriomeningitis virus. J Virol. Jul. 2001;75(13):6204-8. doi: 10.1128/JVI.75.13.6204-6208.2001. PMID: 11390623; PMCID: PMC114337.

(Continued)

*Primary Examiner* — Stacy B Chen
(74) *Attorney, Agent, or Firm* — Bereskin & Parr LLP/S.E.N.C.R.L., s.r.l.; Dominique Lambert

(57) ABSTRACT

Provided herein are fumaric and maleic acid-containing compounds, compositions comprising the same and methods for using such compounds to enhance production, growth, spread or titer of interferon-sensitive viruses in cells, particularly cancer and tumor cells. Also provided are methods of treating tumors or cancers in a subject by administering the compounds and compositions.

18 Claims, 32 Drawing Sheets
Specification includes a Sequence Listing.

(56) References Cited

OTHER PUBLICATIONS

Simm M. The innate cellular responses to HIV-1 invasion: emerging molecules of ancient defense mechanisms. Arch Immunol Ther Exp (Warsz). May-Jun. 2007;55(3):131-8. doi: 10.1007/s00005-007-0023-9. Epub Jun. 8, 2007. PMID: 17557144.

Sandstrom T. S., et al. HIV-Infected Macrophages are Infected and Killed by the Interferon-Sensitive Rhabdovirus MG1. J Virol. Apr. 12, 2021;95(9):e01953-20. doi: 10.1128/JVI.01953-20. PMID: 33568507; PMCID: PMC8104113.

Haralambieva I., et al. Engineering oncolytic measles virus to circumvent the intracellular innate immune response. Mol Ther. Mar. 2007;15(3):588-97. doi: 10.1038/sj.mt.6300076. Epub Jan. 16, 2007. PMID: 17245355; PMCID: PMC3833616.

Young D. F., et al. Mumps virus Enders strain is sensitive to interferon (IFN) despite encoding a functional IFN antagonist. J Gen Virol. Nov. 2009;90(Pt 11):2731-2738. doi: 10.1099/vir.0.013722-0. Epub Jul. 22, 2009. PMID: 19625458; PMCID: PMC2885035.

Elankumaran S., et al. Type I interferon-sensitive recombinant newcastle disease virus for oncolytic virotherapy. J Virol. Apr. 2010;84(8):3835-44. doi: 10.1128/JVI.01553-09. Epub Feb. 10, 2010. PMID: 20147405; PMCID: PMC2849496.

Shimizu K., et al. Sensitivity of rabies virus to type I interferon is determined by the phosphoprotein gene. Microbiol Immunol. 2006;50(12):975-8. doi: 10.1111/j.1348-0421.2006.tb03875.x. PMID: 17179666.

Rudd P., et al. Correlation between interferon sensitivity of reovirus isolates and ability to discriminate between normal and Ras-transformed cells. J Gen Virol. May 2005;86(Pt 5):1489-1497. doi: 10.1099/vir.0.80628-0. PMID: 15831962.

Sharma A., et al. Macaque interferon-induced transmembrane proteins limit replication of SHIV strains in an Envelope-dependent manner. PLoS Pathog. Jul. 1, 2019;15(7):e1007925. doi: 10.1371/journal.ppat.1007925. PMID: 31260493; PMCID: PMC6625738.

Loveys D. A., et al. Role of type I IFNs in the in vitro attenuation of live, temperature-sensitive vaccine strains of human respiratory syncytial virus. Virology. Jun. 5, 2000;271(2):390-400. doi: 10.1006/viro.2000.0290. PMID: 10860892.

Obuchi M., et al. Development of recombinant vesicular stomatitis viruses that exploit defects in host defense to augment specific oncolytic activity. J Virol. Aug. 2003;77(16):8843-56. doi: 10.1128/jvi.77.16.8843-8856.2003. PMID: 12885903; PMCID: PMC167243.

Arnold M. M., et al. Rotavirus antagonism of the innate immune response. Viruses. Dec. 2009;1(3):1035-56. doi: 10.3390/v1031035. Epub Nov. 24, 2009. PMID: 21994581; PMCID: PMC3185539.

Derbyshire J. B. The interferon sensitivity of selected porcine viruses. Can J Vet Res. Jan. 1989;53(1):52-5. PMID: 2492445; PMCID: PMC1255513.

Nakhasi H. L., et al. Rubella virus replication: effect of interferons and actinomycin D. Virus Res. Apr. 1988;10(1):1-15. doi: 10.1016/0168-1702(88)90053-6. PMID: 2453976.

Kartau et al., "Progressive Multifocal Leukoencephalopathy: Current Insights", Degenerative Neurological and Neuromuscular Disease 2019:0 109-121.

"Aminopropionitrile", Wikipedia. (2021).

Extended European Search Report and European Search Opinion received in European patent application No. 18880792.9 dated Oct. 27, 2021.

Selman et al., Dimethyl fumarate potentiates oncolytic virotherapy through NF-kB inhibition, Science Translational Medicine, vol. 10, No. 425, Jan. 24, 2018.

International Search Report received in PCT/CA2018/051492 dated Feb. 20, 2019.

Written Opinion received in PCT/CA2018/051492, dated Feb. 20, 2019.

Ma et al., "Disseminated zoster with paresis in a multiple sclerosis patient treated with dimethyl fumarate", Apr. 3, 2016, p. e203, vol. 3, No. 2, Publisher: Neurol Neuroimmunol Neuroinflamm.

Olagnier et al., "Activation of Nrf2 Signaling Augments Vesicular Stomatitis Virus Oncolysis via Autophagy-Driven Suppression of Antiviral Immunity", Aug. 2, 2017, pp. 1900-1916, vol. 25, No. 8, Publisher: Mol Ther.

Saidu et al., "Dimethyl Fumarate Controls the NRF2/DJ-1 Axis in Cancer Cells: Therapeutic Applications", Mar. 2017, pp. 529-539, vol. 16, No. 3, Publisher: Mol Cancer Ther.

Wu et al., "Dimethyl Fumarate Selectively Reduces Memory T Cells and Shifts the Balance between Th1/Th17 and Th2 in Multiple Sclerosis Patients", Apr. 15, 2017, pp. 3069-3080, vol. 198, No. 8, Publisher: J Immunol.

Chen et al., "Lucidone Suppresses Hepatitis C Virus Replication by Nrf2-Mediated Heme Oxygenase-1 Induction", Antimicrobial Agents and Chemotherapy, pp. 1180-1191, Mar. 2013, vol. 57, No. 3.

Zhang et al., "Antiviral activity of an isatin derivative via induction of PERK-Nrf2-mediated suppression of cap-independent translation", ACS Chem Biol., Apr. 18, 2014;9(4), pp. 1015-1024.

Yu et al., "Sulforaphane Suppresses Hepatitis C Virus Replication by Up-Regulating Heme Oxygenase-1 Expression through PI3K/Nrf2 Pathway", PLoS One, Mar. 29, 2016;11(3):e0152236, pp. 1-23.

Furuya et al., "Sulforaphane Inhibits HIV Infection of Macrophases through Nrf2", PLoS Pathog, Apr. 19, 2016;12(4): e1005581, pp. 1-23.

Kosmider et al., "Nrf2 protects human alveolar epithelial cells against injury induced by influenza A virus", Respiratory Research, 12:43, Jun. 6, 2012, pp. 1-15.

Kesic et al., "Nrf2 expression modifies influenza A entry and replication in nasal epithelial cells", Free Radical Biology & Medicine, 51(2), Jul. 15, 2011, pp. 444-453.

Shoji et al., "Bakuchiol Is a Phenolic Isoprenoid with Novel Enantiomer-selective Anti-influenza A virus Activity Involving Nrf2 Activation", The Journal of Biological Chemistry, vol. 46, Nov. 13, 2015, pp. 28001-28017.

English Translation of Office Action dated Nov. 7, 2023 in respect of Japanese Application No. 2020-501152.

* cited by examiner

A

Dimethyl fumarate (DMF)

B

J

K

A

Diethyl fumarate (DEF)

Diethyl maleate (DEM)

Dimethyl maleate (DMM)

B

Dimethyl fumarate (DMF)

Monomethyl fumarate (MMF)

Fumaric Acid (FA)

Impact of DMF on Influenza A/FM/1/47 titer in VERO-SF cells (ELISA)

3.0X over media
3.8X over vehicle

SEQUENCE LISTING

```
<160> NUMBER OF SEQ ID NOS: 8

<210> SEQ ID NO 1
<211> LENGTH: 20
<212> TYPE: DNA
<213> ORGANISM: Artificial Sequence
<220> FEATURE:
<223> OTHER INFORMATION: gapdh primer

<400> SEQUENCE: 1
acagtcagcc gcatcttctt                                              20

<210> SEQ ID NO 2
<211> LENGTH: 20
<212> TYPE: DNA
<213> ORGANISM: Artificial Sequence
<220> FEATURE:
<223> OTHER INFORMATION: gapdh primer

<400> SEQUENCE: 2
gttaaaagca gccctggtga                                              20

<210> SEQ ID NO 3
<211> LENGTH: 20
<212> TYPE: DNA
<213> ORGANISM: Artificial Sequence
<220> FEATURE:
<223> OTHER INFORMATION: hmox1 primer

<400> SEQUENCE: 3
actgcgttcc tgctcaacat                                              20

<210> SEQ ID NO 4
<211> LENGTH: 20
<212> TYPE: DNA
<213> ORGANISM: Artificial Sequence
<220> FEATURE:
<223> OTHER INFORMATION: hmox1 primer

<400> SEQUENCE: 4
ggggcagaat cttgcacttt                                              20
```

```
<210> SEQ ID NO 5
<211> LENGTH: 20
<212> TYPE: DNA
<213> ORGANISM: Artificial Sequence
<220> FEATURE:
<223> OTHER INFORMATION: nrf2 primer

<400> SEQUENCE: 5
caactactcc caggttgccc                                           20

<210> SEQ ID NO 6
<211> LENGTH: 20
<212> TYPE: DNA
<213> ORGANISM: Artificial Sequence
<220> FEATURE:
<223> OTHER INFORMATION: nrf2 primer

<400> SEQUENCE: 6
agtgactgaa acgtagccga                                           20

<210> SEQ ID NO 7
<211> LENGTH: 20
<212> TYPE: DNA
<213> ORGANISM: Artificial Sequence
<220> FEATURE:
<223> OTHER INFORMATION: ifitm1 primer

<400> SEQUENCE: 7
ccgtgaagtc tagggacagg                                           20

<210> SEQ ID NO 8
<211> LENGTH: 20
<212> TYPE: DNA
<213> ORGANISM: Artificial Sequence
<220> FEATURE:
<223> OTHER INFORMATION: ifitm1 primer

<400> SEQUENCE: 8
ggtagactgt cacagagccg                                           20
```

COMPOSITIONS AND METHODS FOR ENHANCING PRODUCTION, GROWTH, SPREAD, OR ONCOLYTIC AND IMMUNOTHERAPEUTIC EFFICACY OF INTERFERON-SENSITIVE VIRUSES

FIELD OF INVENTION

The present invention relates to compounds, methods, and compositions that enhance interferon-sensitive virus production, infection, growth, and/or spread, and/or potentiate the oncolytic and immunotherapeutic activity of oncolytic viruses.

BACKGROUND OF THE INVENTION

Genetically attenuated viruses form the basis of a growing number of biotechnology and pharmaceutical platforms. Genetically attenuated viruses can be generated either from direct genetic engineering or indirectly by genetic selection. For example, but not meant to be limiting, attenuation can be species specific wherein a virus adapted for growth in one host by serial passaging (e.g. eggs) leads to maladaptation and consequent attenuation in another host (e.g. humans). Similarly, genetic selection of viruses can be carried out in a cancer cell, rendering the virus maladapted for replication in a normal cell. Such a replicating virus adapted or genetically engineered for attenuation in normal cells but optimally growing in cancer cells is often referred to as an oncolytic virus. Often, attenuation will involve the incapacity of the selected or engineered virus to overcome the intended host cell's antiviral defense mechanisms, a key mediator of which is the antiviral cytokine interferon (IFN). There exists a broad range of attenuated viruses and these are used for multiple applications and purposes. This includes viral strains rendered safe for the production of either live attenuated or inactivated vaccines (e.g. influenza, modified vaccinia ankara). This also includes viral vectors rendered replication incompetent from either partial (e.g. Adenovirus) or complete removal of viral genes (e.g. Lentiviruses or retroviruses), making the virus dependent on supplementation of essential viral genes/functions in trans (e.g. expression of viral proteins from co-transfected plasmids). These viruses are often used as vectors for gene therapy, where the vector carries some form of therapeutic transgene. A non-replicating virus, also referred to as a replication incompetent virus or a replication defective virus, is defined as a virus that can be produced from a first cell, assisted by non-viral components such as, for example but not limited to, plasmids, that ultimately leads to the formation of virus particles that can infect a second cell, but that cannot subsequently replicate the second cell.

Emerging in the field of cancer therapeutics, oncolytic virotherapy has shown significant promise over the last decade. A number of oncolytic viruses (OV) based on a wide range of viral backbones from small RNA viruses (e.g. rhabdoviruses), to large DNA viruses (e.g. poxviruses, herpesviruses) are currently being evaluated in clinical trials to treat a range of cancer types. Generating substantial excitement for this form of cancer therapy, approval of the first-in-class OV based on herpes-simplex virus-1 (HSV-1) for treatment of melanoma was granted by the FDA in 2015.

Oncolytic viruses (OVs) are self-amplifying biotherapeutic agents that have been selected or engineered to preferentially infect and kill cancer cells. When effective, OVs lead to tumor eradication not only by direct lysis of cancer cells but also through downstream generation of anti-cancer immune responses, vascular shutdown, and therapeutic transgene expression. For this reason, they are considered as immunotherapeutics. As a basis for their cancer selectivity, OVs exploit cellular defects that are inherent to the cancerous phenotype. This includes dysfunctional anti-viral responses such as type 1 interferon response, immune evasion, increased cell proliferation and metabolism, and leaky tumor vasculature. The biological environment ensuing from tumorigenesis is well suited to support the growth of genetically attenuated OVs that are otherwise harmless to normal cells.

OVs stand to be an attractive therapeutic modality for cancer because of their curative potential and their relatively mild side effects amounting to acute flu-like symptoms. However, heterogeneity in the clinical response to OVs remains a significant hurdle to overcome, as demonstrated in several human clinical trials. This heterogeneity in response may be attributed to factors that impede effective OV delivery and spread within tumors.

Although attenuated viruses and oncolytic viruses can and do work as single agents, numerous studies have shown that viral spread, overall efficacy and/or oncolysis can be improved using pharmacological compounds [1-3]. Beyond oncolytic effects on tumor cells, OVs can also boost anti-tumor immunity by directing immune responses to the tumor [4-7]. This immunostimulatory effect can be further enhanced by integrating immune stimulatory genes into the viral genome[6-9], such as T-VEC, a herpes simplex virus type 1 based OV recently approved for treatment of melanoma by the US Food and Drug Administration (FDA) [10-12]. Combinations of OVs and other forms of immunotherapy have now emerged as a promising approach in human patients [5-7].

Fumaric acid esters (FAE), such as dimethylfumarate (DMF), are ester derivatives of fumaric acid [13]. Fumaric acid is an intermediate in the citric acid cycle, which is a basic cellular process that generates energy in the mitochondria. Fumaric acid esters (FAE) are a class of compounds with known anti-inflammatory and neuroprotective effects [14, 15, 17]. The mechanisms involved have yet to be fully elucidated, but is thought to be mediated through the activation of the antioxidative transcription factor nuclear factor (erythroid-derived 2)-like 2 (NRF2) pathway [15], the inhibition of NF-κB [16] as well as functional depletion of glutathione (GSH) [18-19].

FAEs (marketed as Fumaderm®, Psorinovo®) were first approved as a treatment for psoriasis in Germany. Recently, dimethyl fumarate (DMF), an FAE marketed as Tecfidera®, was approved by the U.S. Food and Drug Administration (FDA) and the European Medicines Agency for the treatment of relapsing forms of multiple sclerosis and relapsing-remitting multiple sclerosis [20]. Clinical studies on the long-term use of DMF have not revealed any severe long-term adverse effects [20-22]. Recent reports suggest that DMF has anticancer potential, shown to suppress tumor growth and metastasis [23-28] in addition to sensitizing tumors to chemotherapy [26, 29]. Furthermore, DMF is currently under clinical evaluation for the treatment of Chronic Lymphocytic Leukemia and Cutaneous T Cell Lymphoma (e.g. NCT02546440, NCT02784834).

There is a need in the art to identify compounds and compositions that enhance virus growth and spread. There is also a need in the art to identify compounds and compositions that enhance virotherapy anti-cancer efficacy. Further, there is a need in the art to identify novel methods for treating cancer cells in vitro and/or in vivo.

SUMMARY OF THE INVENTION

The present invention relates to compositions and methods that enhance interferon-sensitive virus production, infection, growth, and/or spread, and/or potentiate the oncolytic and/or immunotherapeutic activity of oncolytic viruses.

Results described herein observed one or more previously unreported effects of Fumaric and Maleic Acid Esters (FMAEs): an ability to enhance the production, infection, growth and/or spread of replicating and non-replicating interferon-sensitive viruses; and to increase the therapeutic efficacy of oncolytic viruses, for example in otherwise resistant cancers, which may involve inhibiting the innate antiviral response of cancer cells.

In an embodiment, there is provided herein a method of enhancing or increasing the production, growth, infection, spread, or titer, of an interferon-sensitive virus in an immortalized cell, cancer cell or tumor cell, comprising administering a FMAE compound to the cell prior to, concurrently with, or after infection of the immortalized, cancer or tumor cell with the interferon-sensitive virus.

In another embodiment, there is provided herein a method of enhancing, increasing or potentiating the production, infection, spread, titer, or the oncolytic activity of an oncolytic virus in cancer or tumor cells, comprising administering one or more FMAE-containing compounds selected from the group consisting of:
Dimethylfumarate (DMF), diethylfumarate (DEF), dimethyl maleate (DMM), diethyl maleate (DEM), monoethyl maleate, monomethyl maleate, monoethyl fumarate, monomethyl fumarate (MMF), and derivatives thereof.

In certain embodiments, compounds for viral enhancement may include those defined by formula (I), (II), a combination thereof, fumaric acid esters or maleic acid esters, pharmaceutically acceptable addition salts thereof, or racemic or stereochemically isomeric forms thereof, wherein R1 and R2 may be the same or different and may be independently selected from, for example, OH, O$^-$, and (C$_{1-6}$)alkoxy, or a pharmaceutically acceptable salt thereof.

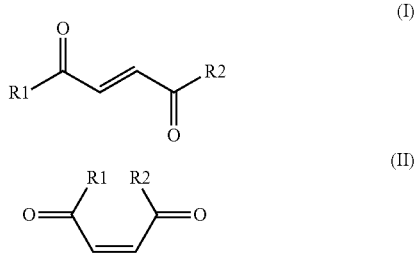

In another non-limiting embodiment, compounds for viral enhancement may include one or more compounds defined by formula (I) and/or (II), wherein R1 and R2 which may be the same or different and may be independently selected from a linear, branched or cyclic, saturated or unsaturated (C$_{1-2}$)alkoxy, or (C$_{3-20}$)alkoxy, and wherein said radicals may optionally be substituted with halogen, hydroxy, (C$_{1-4}$) alkyl, nitro or cyano, for example.

In certain non-limiting embodiments, compounds of Formulae (I) and/or (II) may also exist in several tautomeric forms including the enol form, the keto form, and mixtures thereof. Accordingly, the chemical structures depicted herein encompass all possible tautomeric forms.

In a non-limiting embodiment, compounds selected from a compound of Formulae (I) and/or (II) may include isotopically labeled compounds, where one or more atoms have an atomic mass different from the atomic mass conventionally found in nature. Examples of isotopes that may be incorporated into the compounds disclosed herein include, but are not limited to, 2H, 3H, 11C, 13C, 14C, 15N, 18O, 17O, etc.

In another non-limiting embodiment, example compounds may include compounds defined by formula (I) and/or (II), wherein R1 and R2 are both OH, or O$^-$.

In certain embodiments, compounds as described herein, or combinations of one or more compounds as described herein, or compositions comprising at least one compound as described herein, may be administered to cells prior to, or concurrently with, or following infection of the cells with the virus. Subsequently, the cells, one or more compounds and virus may be grown or cultured.

In still another embodiment of any one of the method or methods described herein, the FMAE-containing compound or combination of compounds may be present in a composition comprising the compound(s) and one or more of a carrier, diluent or excipient.

In another embodiment, there is provided herein a composition comprising one or more FMAE-containing compounds, and one or more of a) an interferon-sensitive virus, a genetically modified interferon sensitive virus, an attenuated interferon-sensitive virus, an oncolytic interferon-sensitive virus, an interferon-sensitive virus-based cancer vaccine or cancer gene therapy vector, b) one or more cancer cells, c) a pharmaceutically acceptable carrier, diluent or excipient, d) non-cancer cells; e) cell culture media; f) one or more cancer therapeutics; or any combination of a)-f). The present invention also contemplates embodiments wherein any one or a combination of a)-f) are specifically excluded from the composition or kit. Any component or group of components may be excluded if desired.

In yet another embodiment, there is provided herein a kit comprising one or more of FMAE-containing compounds, and one or more of a) an interferon-sensitive virus, a genetically modified interferon-sensitive virus, an attenuated interferon-sensitive virus, an oncolytic interferon-sensitive virus, an interferon-sensitive virus-based cancer vaccine or cancer gene therapy vector, b) one or more cancer cells, c) a pharmaceutically acceptable carrier, diluent or excipient, d) non-cancer cells; e) cell culture media; f) one or more cancer therapeutics, g) a cell culture plate or multi-well dish; h) an apparatus to deliver the compound to a cell, medium or to a subject; i) instructions for using the compound or any component in the kit, of a)-i). The present invention also contemplates kits wherein any one or a combination thereof of a)-i) are specifically excluded.

In another embodiment, the cells may be cancer cells in vivo, or in vitro.

In a further embodiment, the in vivo cancer cells may be from a mammalian subject.

In still a further embodiment, the mammalian subject may be a human subject.

In another embodiment, the cells may be non-cancer cells in vitro.

In yet another embodiment, there is provided herein a method of increasing the oncolytic activity of an oncolytic interferon-sensitive oncolytic virus in cancer or tumor cells, comprising administering a FMAE-containing compound, or a combination of FMAE containing compounds to said cancer or tumor cells prior to, concurrently with or after the oncolytic virus.

In another embodiment, the cancer or tumor cells may be in vivo, or in vitro.

In still another embodiment, the in vivo cancer or tumor cells may be from a mammalian subject.

In yet another embodiment, the mammalian subject is a human subject.

In another embodiment, there is provided herein a use of FMAE-containing compounds in the manufacture of a medicament for enhancing or increasing the infection, spread, titer, cytotoxicity or immunotherapeutic activity of an oncolytic interferon-sensitive virus in cancer or tumor cells.

In yet another embodiment, in any of the compositions or methods described above or herein throughout, the FMAE-containing compound enhances or increases interferon-sensitive virus infection, growth, spread or any combination thereof in infection-resistant cells.

In yet another embodiment, in any of compositions or methods described above or herein throughout, the FMAE-containing compound enhances or increases interferon-sensitive virus infection, growth, spread or any combination thereof in cancer cells or tumors in vivo without inducing virus spread to major organs.

In a further embodiment, in any of compositions or methods described above or herein throughout, the FMAE-containing compound enhances virally induced cancer cell death in vivo and/or in vitro.

In an embodiment of any of the methods as described herein or throughout, the interferon-sensitive virus may be any suitable virus known in the art which is interferon-sensitive or which is rendered interferon-sensitive, examples including, but not limited to, replicating or non-replicating viruses, such as: newcastle disease virus, polio virus, mumps virus, measles virus, influenza virus, Maraba virus (such as MG-1), Rabies virus, Rotavirus, Hepatitis A virus, Rubella virus, Dengue virus, Chikungunya virus, Respiratory Syncitial Virus, LCMV, lentivirus, replicating retrovirus, adenovirus, herpes simplex virus or rhabdovirus, or a variant or derivative thereof.

In an embodiment of any method described above or herein, the interferon-sensitive virus is an oncolytic interferon-sensitive virus. Representative example may be any suitable oncolytic virus known in the art which preferentially infects and lyses cancer or tumor cells as compared to non-cancer or normal cells. Examples of viruses known in the art which may be engineered to be used as oncolytic viruses may be employed herein and include, without limitation, reovirus, newcastle disease virus, polio virus, mumps virus, measles virus, influenza virus, rhabdoviruses such as vesicular stomatitis virus, adenovirus, herpes simplex virus and derivatives/variants thereof. In a preferred embodiment, the virus is a Vesicular stomatitis virus (VSV), or a related rhabdovirus variant/derivative thereof for example, selected under specific growth conditions, one that has been subjected to a range of selection pressures, one that has been genetically modified using recombinant techniques known within the art, or a combination thereof. In another preferred embodiment, the virus may be VSVΔ51 [30]. Other derivatives or variants may be based on viruses such as Maraba (MG-1, for example), Rabies, Rotavirus, Influenza, Hepatitis A, Mumps, Measles, Rubella, Reovirus, Dengue Virus, Chikungunya Virus, Respiratory Syncitial Virus, LCMV, lentivirus, or replicating retrovirus, for example.

In one embodiment of any methods above or described herein throughout, the one or more types of immortalized cells may be immortalized cells in vitro or in vivo from any cell, cell line, tissue or organism, not limited to, human, rat, mouse, cat, dog, pig, primate, horse and the like, for example, without limitation: Vero, HEK-293 cells, EB-66 cells, EbX cells, PER.C6 cells, AGE1.CR, Age1.CS, Age1.HN, Age1.RO, QOR2/2E11, UMNSAH-DF1, CHO, hybridoma cells, sf9 cells, or R4 cells.

In another embodiment, the one or more types of cancer or tumor cells may be cancer or tumor cells in vitro or in vivo from any cell, cell line, tissue or organism, for example, but not limited to human, rat, mouse, cat, dog, pig, primate, horse and the like, for example tumor forming cells such as, but not limited to 293-T cells, BHK21 cells, or MDCK cells.

In a preferred embodiment, the one or more cancer or tumor cells comprise human cancer or tumor cells, for example, but not limited to lymphoblastic leukemia, myeloid leukemia, adrenocortical carcinoma, AIDS-related cancers, AIDS-related lymphoma, anal cancer, appendix cancer, astrocytoma, atypical teratoid/rhabdoid tumor, basal cell carcinoma, bile duct cancer, bladder cancer, bone cancer, osteosarcoma, malignant fibrous histiocytoma, brain stem glioma, brain tumor, cerebellar astrocytoma, cerebral astrocytoma/malignant glioma, craniopharyngioma, ependymoblastoma, medulloblastoma, pineal parenchymal tumors of intermediate differentiation, supratentorial primitive neuroectodermal tumors and pineoblastoma, visual pathway and hypothalamic glioma, spinal cord tumors, breast cancer, bronchial tumors, Burkitt lymphoma, carcinoid tumor, central nervous system lymphoma, cervical cancer, chordoma, chronic lymphocytic leukemia, chronic myelogenous leukemia, chronic myeloproliferative disorders, colon cancer, cutaneous T-Cell lymphoma, embryonal tumors, endometrial cancer, ependymoblastoma, ependymoma, esophageal cancer, extracranial germ cell tumor, extragonadal germ cell tumor, extrahepatic bile duct cancer, eye cancer, intraocular melanoma, retinoblastoma, gallbladder cancer, gastric (stomach) cancer, gastrointestinal carcinoid tumor, gastrointestinal stromal tumor (GIST), gastrointestinal stromal cell tumor, germ cell tumors, extracranial, extragonadal, ovarian, gestational trophoblastic tumor, glioma, hairy cell leukemia, head and neck cancer, hepatocellular (Liver) cancer, histiocytosis, Langerhans cell cancer, Hodgkin lymphoma, hypopharyngeal cancer, islet cell tumors, Kaposi sarcoma, kidney cancer, laryngeal cancer, lymphocytic leukemia, hairy cell leukemia, lip and oral cavity cancer, liver cancer, non-small cell lung cancer, small cell lung cancer, Hodgkin lymphoma, non-Hodgkin lymphoma, malignant fibrous histiocytoma of bone and osteosarcoma, medulloblastoma, medulloepithelioma, melanoma, intraocular melanoma, Merkel cell carcinoma, mesothelioma, metastatic squamous neck cancer, mouth cancer, multiple endocrine neoplasia syndrome, multiple myeloma/plasma cell neoplasm, nasal cavity and paranasal sinus cancer, nasopharyngeal cancer, neuroblastoma, oral cancer, oropharyngeal cancer, ovarian cancer, pancreatic cancer, parathyroid cancer, penile cancer, pharyngeal cancer, pheochromocytoma, pineal parenchymal tumors, pineoblastoma and supratentorial primitive neuroectodermal tumors, pituitary tumor, plasma cell neoplasm/multiple myeloma, pleuropulmonary blastoma, primary central nervous system lymphoma, prostate cancer, rectal cancer, renal cell (kidney) cancer, renal pelvis and ureter cancer, transitional cell cancer, respiratory tract carcinoma, retinoblastoma, rhabdomyosarcoma, salivary gland cancer, uterine sarcoma, skin cancer, Merkel cell skin carcinoma, small intestine cancer, soft tissue sarcoma, squamous cell carcinoma, squamous neck cancer, stomach (Gastric) cancer, supratentorial primitive neuroectodermal tumors, T-Cell lymphoma, testicular cancer, throat cancer, thymoma and thymic carcinoma, thyroid cancer, trophoblastic tumor, urethral cancer, uterine cancer, endometrial cancer, uterine sarcoma, vaginal cancer, vulvar cancer, or Wilms tumor. However, the compounds and compositions described herein possible may be used to treat other cancers or tumors in vivo or in vitro.

The present invention also provides a composition comprising the FMAE-containing compound(s) as described herein, and an acceptable carrier, diluent or excipient. In a further embodiment, the carrier is a pharmaceutically acceptable carrier.

Also provided is a method of enhancing or increasing the infection, spread and/or titer, and/or cytotoxicity of a virus in cells, the method comprising, administering the FMAE-containing compound(s) as described herein to the cells prior to, after or concurrently with the virus, and culturing the virus and cells to enhance or increase the infection, spread and/or titer, or cytotoxicity of the virus in said cells. Preferably, the cells are cancer cells, tumor cells or cells which have been immortalized. More preferably, the cells are in vivo cancer cells from a mammalian, still more preferably a human subject and the method is practiced in vivo. In another separate embodiment, the cells are in vitro immortalized cells.

Also provided is a method of enhancing or increasing the oncolytic activity of an oncolytic virus in cancer cells comprising, administering the compound(s) as described herein to the cancer cells or subject prior to, concurrently with or after the oncolytic virus and culturing the oncolytic virus and cancer cells. In a further embodiment, the cancer cells are in vivo cancer cells. In a separate embodiment, the cancer cells are in vitro cancer cells. The cells may be from a mammalian subject, preferably a human subject.

In a particular embodiment, which is not meant to be limiting in any manner, there is provided a kit comprising a FMAE-containing compound and a medium for growing, culturing or infecting cells with a virus and optionally, one or more cells which are capable of being infected by the virus, and/or one or more viruses. The kit may also comprise instructions for using any component or combination of components and/or practicing any method as described herein.

The present invention also provides a method of enhancing or increasing the infection, spread and/or titer, or oncolytic activity of a virus in cells comprising, administering a FMAE-containing compound as described herein to the cells prior to, after or concurrently with the virus. The method may be practiced in vivo or in vitro.

The present invention also provides a method of enhancing or increasing the spread of an oncolytic virus in tumor or cancer cells comprising, administering a compound as described above to the cancer or tumor cells prior to, after or concurrently with the oncolytic virus. The cancer or tumor cells may be in vivo, or in vitro, preferably in vivo from a mammalian subject such as, but not limited to, a human subject.

Also provided is a method of enhancing or increasing the oncolytic activity of an oncolytic virus in cancer or tumor cells comprising, administering a compound as described above to the cancer or tumor cells prior to, concurrently with or after the oncolytic virus. The cancer or tumor cells may be in vivo, or in vitro, preferably from a mammalian subject such as, but not limited to a human subject.

The present invention also contemplates a method of producing a virus by growing the virus in an appropriate medium in the presence of a FMAE-containing compound as described above.

The present invention also contemplates a method of producing an attenuated interferon-sensitive virus by growing the virus in an appropriate medium in the presence of a FMAE-containing compound as described above.

The present invention also contemplates a method of producing a genetically modified virus by growing the virus in an appropriate medium in the presence of a FMAE-containing compound as described above.

The present invention also contemplates a method of producing an oncolytic virus by growing the virus in an appropriate medium in the presence of a FMAE-containing compound as described above.

The present invention also contemplates a method of producing a live virus vaccine by growing the virus in an appropriate medium in the presence of a FMAE-containing compound as described above.

The present invention also contemplates a method of producing a virus-based gene therapy vector by growing the virus in an appropriate medium in the presence of a FMAE-containing compound as described above.

This summary of the invention does not necessarily describe all features of the invention.

BRIEF DESCRIPTION OF THE DRAWINGS

These and other features of the invention will become more apparent from the following description in which reference is made to the appended drawings wherein:

FIG. 8 shows the impact of DMF on influenza A/FM/1/47 titer in VERO-SF cells by ELISA. VeroSF cells (Vero cells adapted to serum free media) were seeded in 96 well plates and treated with vehicle alone, DMF and infected with Influenza A/FM/1/47 at MOI 0.01. 3 days later, infectious supernatant was collected and pooled (N=3 wells per condition) and subject to ELISA (Cat #IAV142, Virusys) where absorbance values were converted to pfu/ml based on a standard curve generated from a FM/1/47 stock previously titered by plaque assay. Data represents average of 2-4 experiments.

DETAILED DESCRIPTION

Figure 1:
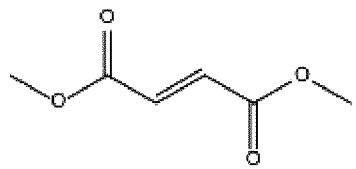
FIG. 1 shows that DMF enhanced virus infection and oncolytic activity in cancer cell lines. (A) Structure of dimethyl fumarate. (B-F) Resistant human renal cancer cell lines 786-0, (B, D) and various human and murine cell lines were pretreated with DMF for 4 hours and subsequently infected with (B-D) VSVΔ51 (MOI: 0.01), (E) HSV (MOI: 0.01), or (F) Sindbis (MOI:10). (B) 24 hours post infection fluorescent images were taken of the infected cancer cells. (C-F) Corresponding viral titer were determined 48 hours post infection from supernatants. (N=3-4; Error bars indicate SD (standard deviation); (D-F) 2-tailed t-test; $p<0.05$ as compared to the untreated counterpart for each cell line; (C) One-way ANOVA; *$p<0.05$, *** $p<0.001$, as compared to the untreated condition counterpart). (G) Human tumor cell line A549 pretreated as in (B) and infected with an adenovirus expressing firefly luciferase (Ad5) at an MOI of 1. Luciferase activity was measured over the course of 7 days. Results are represented as relative light units and background is indicated by black line. (N=3; Error bars indicate SD; Significance enhancement for day 2 to 5, $p<0.05$ by two-way ANOVA). (H) Multi-step, and single-step growth curve of 786-0 pretreated with DMF and infected with VSVΔ51 MOI: 0.001, 0.01 or 3; supernatants were titered by plaque assay (N=3; Error bars indicate SD). (I) 786-0 were pretreated with DMF for 4 hours and infected with VSVΔ51 (MOI: 0.0001), an agarose overlay was added after 1 hour of infection. Fluorescence microscopy of a representative plaque 48 hour after infection. Corresponding image of coomassie blue stain of the full well and average plaque diameter illustrating the enhancement of the plaque diameters in presence of DMF (N=20; Bars indicate mean; 1 way ANOVA; *$p<0.05$, * $p<0.001$, as compared to the mock condition counterpart). (J) 786-0, CT26WT and B16F10 cell lines were pretreated and infected as in (B). Cell viability was assayed 48 hours post infection. Results were normalized to the average of the values obtained for the corresponding uninfected, untreated cells (N=8; Error bars indicate SD; *p<0.001 by 1 way ANOVA; as compared to VSVΔ51 condition). (K) 786-0 cells treated with 150 μM of DMF at various time pre or post infection with VSVΔ51 (MOI: 0.01) or mock untreated, supernatants were collected 24 hours post infection, and titered by plaque assay (N=3; Error bars indicate SD; 2-tailed t-test; * p<0.05, ** p<0.01, as compared to the mock condition counterpart).
Figure 1:
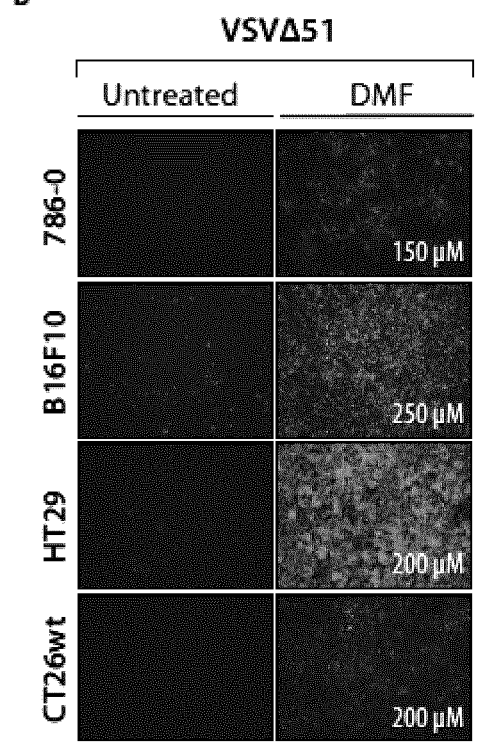
Figure 1:
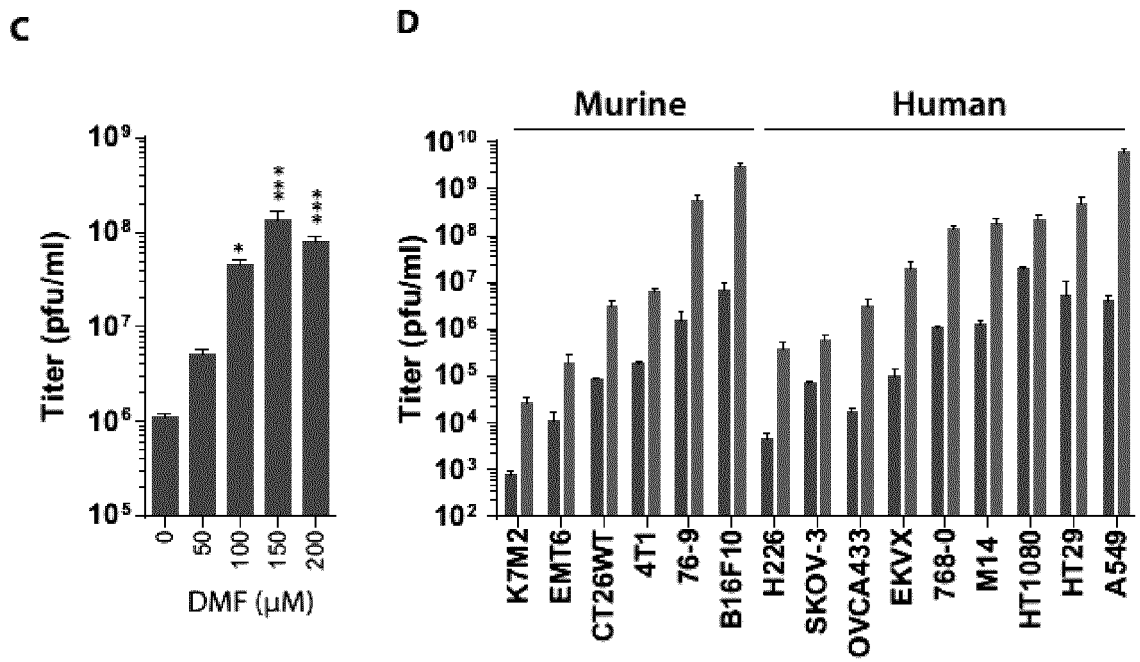
Figure 1:
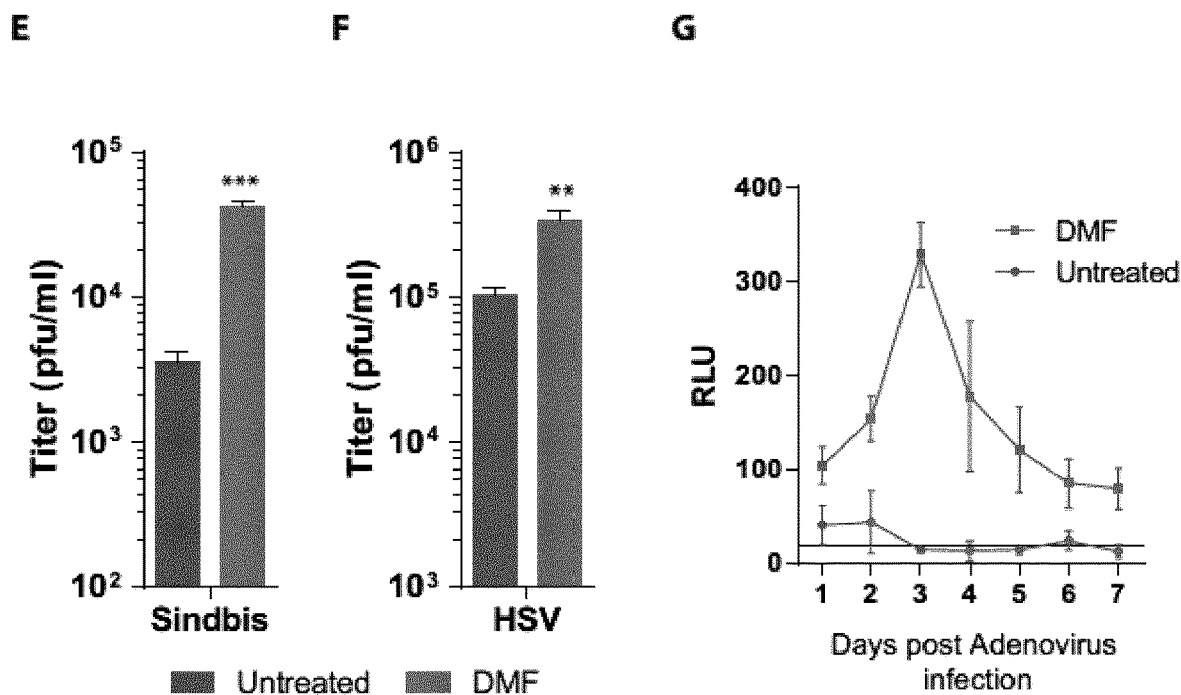
Figure 1:
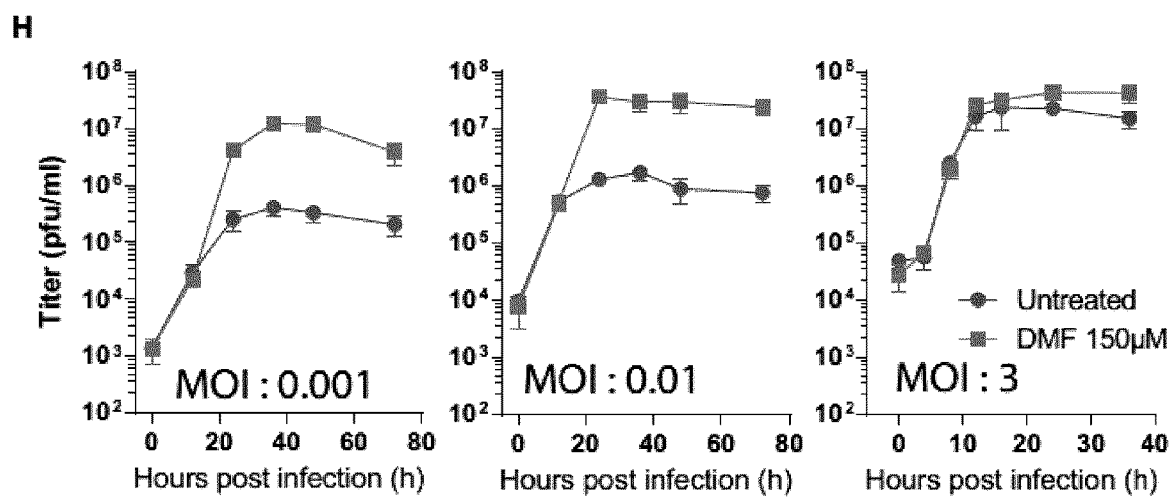
Figure 1:
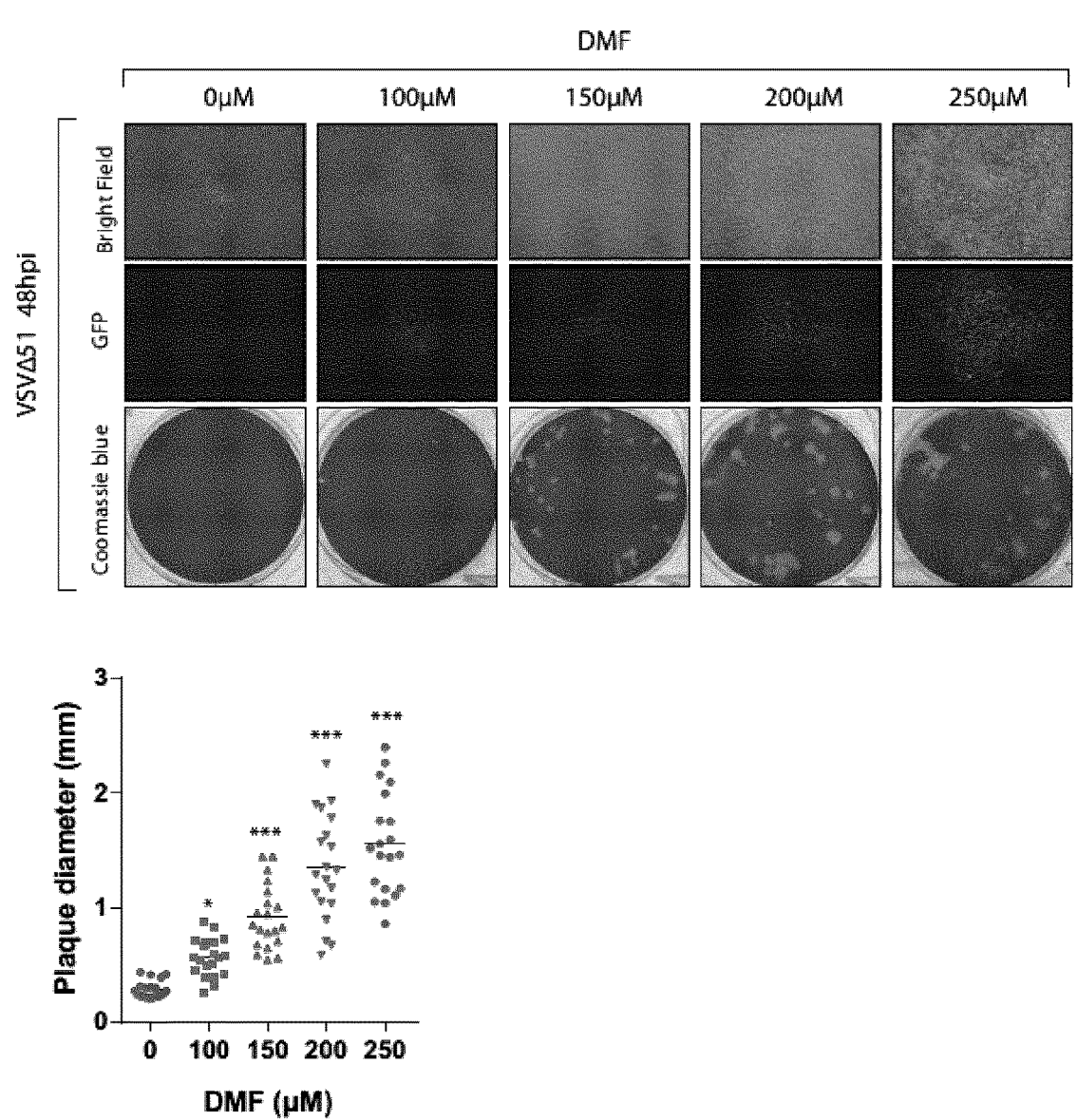
Figure 1:
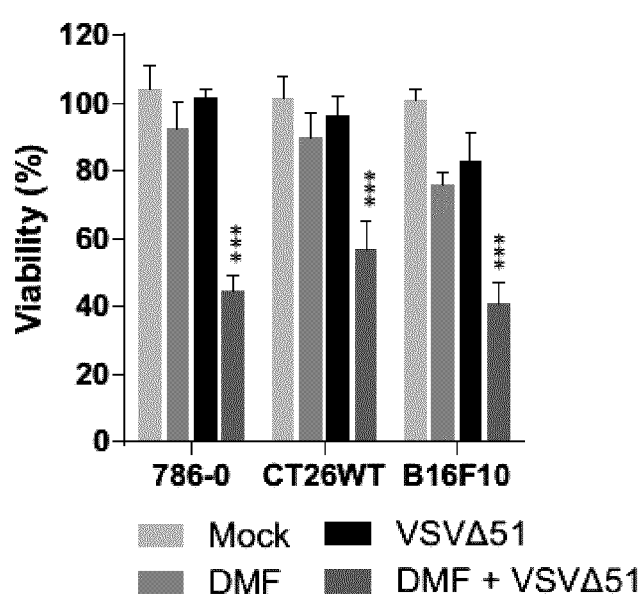
Figure 1:
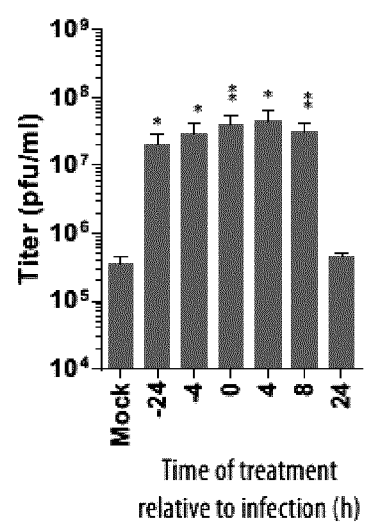
Figure 2:
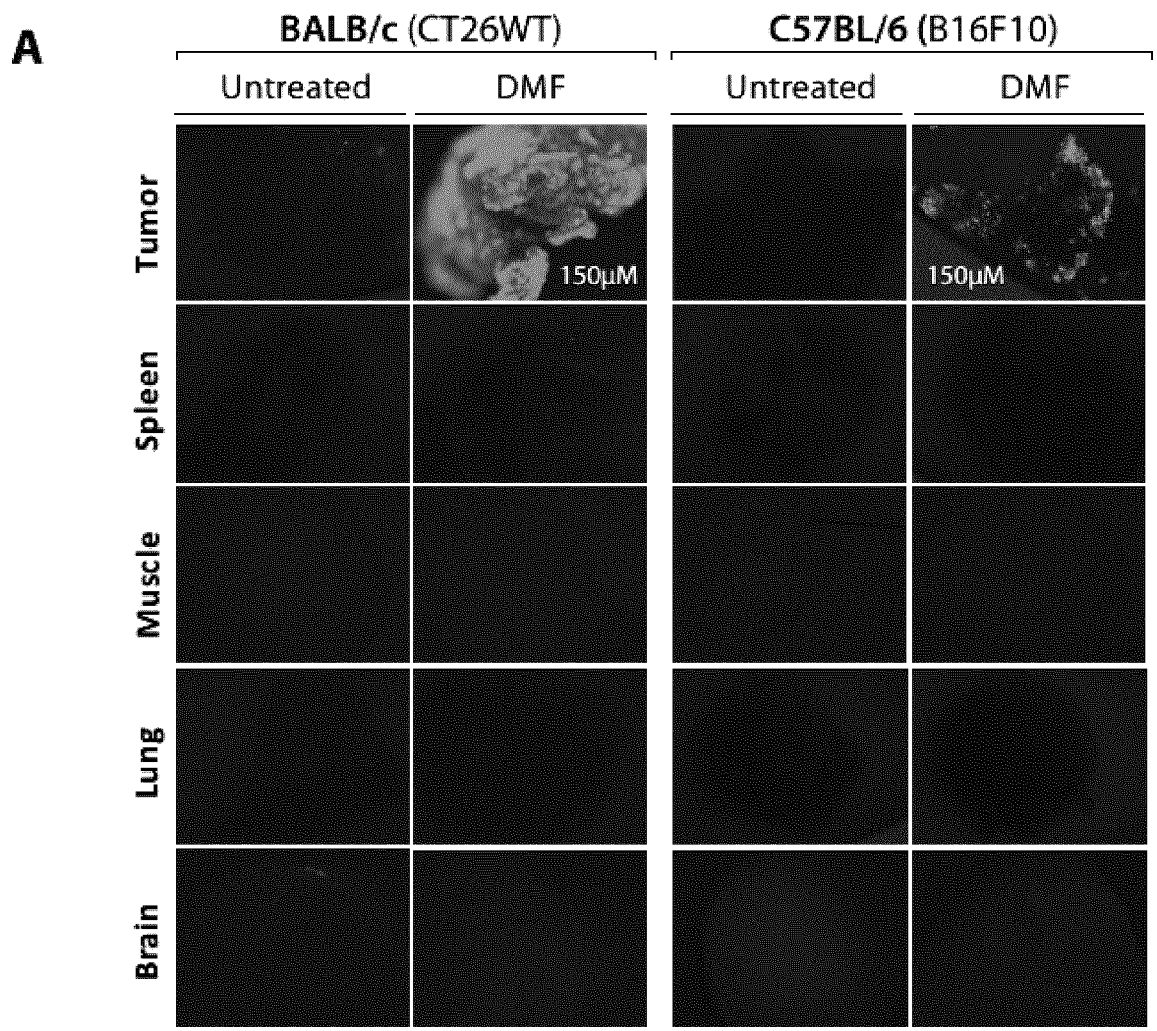
FIG. 2 shows that DMF selectively enhanced infection of oncolytic virus in ex vivo and human clinical samples. (A, B) CT26WT and B16F10 tumors were grown subcutaneously in BALB/c and C57BL/6 mice respectively and excised. BALB/c and C57BL/6 mice spleen, muscle, lung, and brain tissue were also collected, and cored. Tumor and normal tissue cores were pretreated with 150 μM of DMF for 4 hours and subsequently infected with $1 \times 10^4$ PFU of oncolytic VSVΔ51 expressing GFP. (C-D) Human tumor tissue cores, (F) human normal tissue cores or (E) patient derived cell lines were treated with DMF for 4 hours, and subsequently infected with (C-D, F) $1 \times 10^4$ PFU or (E) at an MOI of 0.01 of oncolytic VSVΔ51 expressing GFP. (A, D) 24 hours post infection fluorescent images were acquired of the tumor or normal tissue cores. Representative images from each triplicate set are shown. (B, C, E, F) Viral titers were determined 48 hours post infection (N=3-4; Error bars indicate SD; 2-tailed t-test; ns, no statistical significance; *p<0.05, p<0.01, *p<0.001, as compared to the untreated counterpart).
Figure 2:
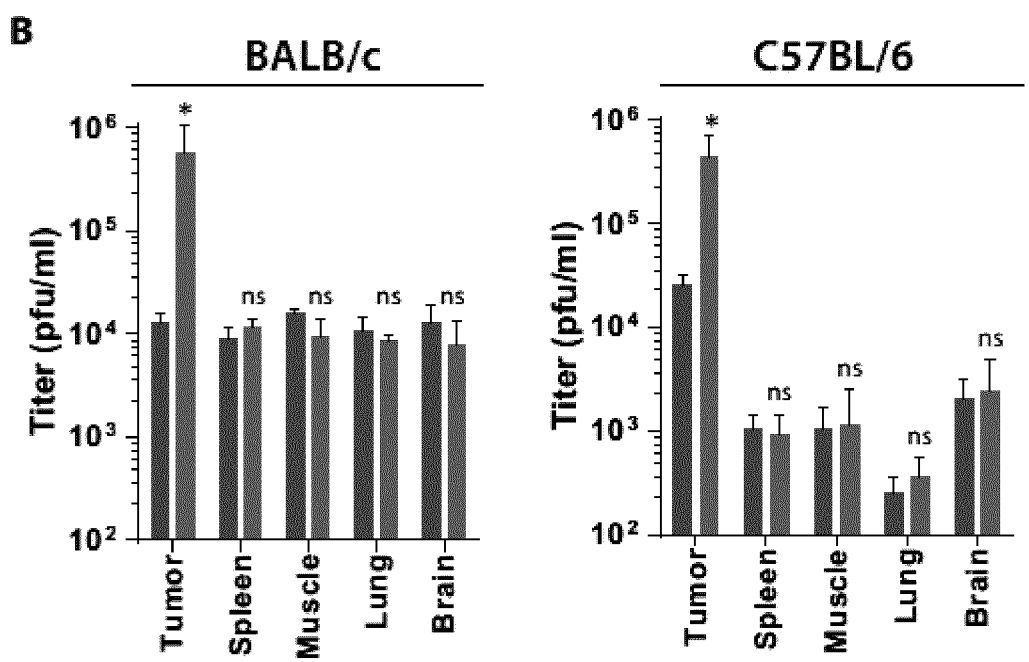
Figure 2:
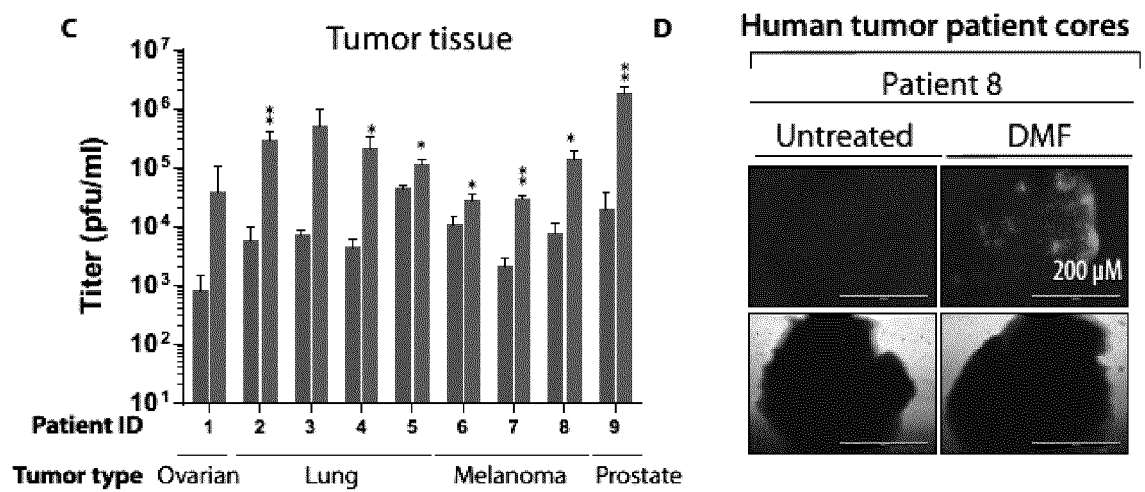
Figure 2:
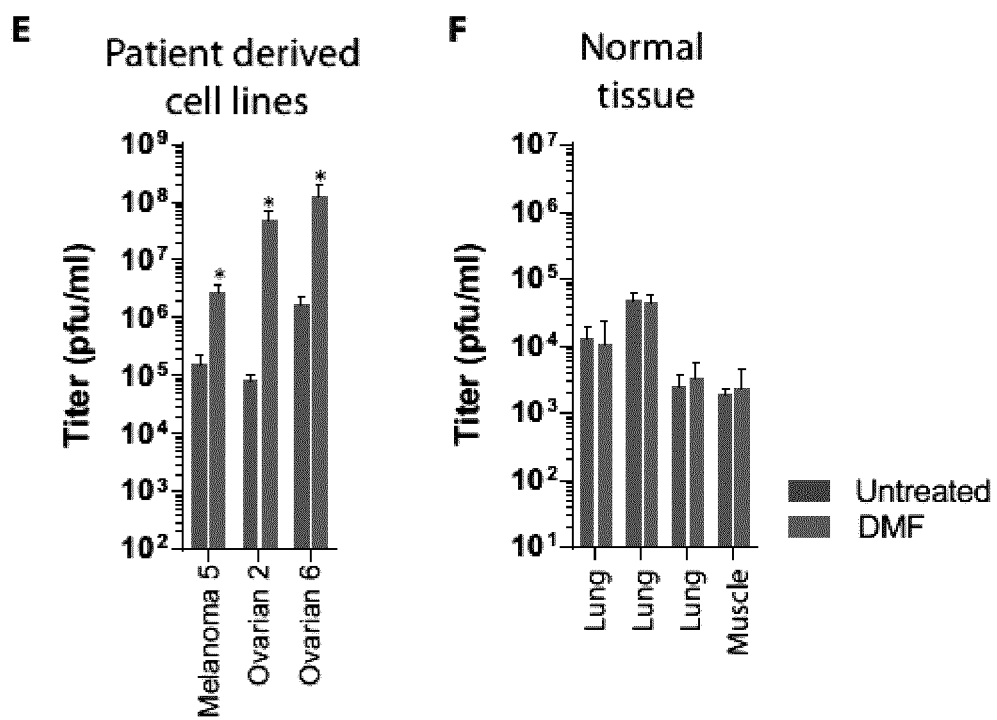

The following description is of one or more preferred embodiments. Several inventions may be described herein with compositions, and kits provided with identical, similar or distinct uses or methods of use.

In a first aspect, there is provided herein a method of enhancing or increasing one or more of the production, infection, spread, or titer, and/or the oncolytic or immunotherapeutic activity of an interferon-sensitive virus in a cell, the method comprising administering a FMAE-containing compound to said cells prior to, after, or concurrently with infection of the cells with the virus.

In another aspect, which is not meant to be limiting, there is provided herein a method of enhancing or increasing the production, infection, spread, titer of an interferon-sensitive virus in immortalized cells, in vitro, the method comprising administering a FMAE-containing compound to said cells prior to, after, or concurrently with infection of the cells with the virus.

In a further aspect, which is not meant to be limiting, the interferon-sensitive virus production, infection, spread, titer is potentiated as compared to the infection, spread, titer of the virus in the absence of the FMAE-containing compound.

In a further aspect there is provided herein a method of enhancing or increasing the production, infection, spread, titer, or the oncolytic or immunotherapeutic activity of an oncolytic interferon-sensitive virus in cancer cells or tumor cells, the method comprising administering a FMAE-containing compound to said cells prior to, after, or concurrently with infection of the cells with the virus.

In a further aspect, which is not meant to be limiting, the oncolytic virus oncolytic activity is potentiated in cancer or tumor cells as compared to the oncolytic activity of the virus alone or the therapeutic activity of the FMAE-containing compound alone.

In yet another embodiment of any of the compositions, method or methods described above, the FMAE-containing compound enhances interferon-sensitive virus infection, growth or spread in infection-resistant cells.

The present disclosure contemplates viral enhancement as meaning that the result of the treatment is an increase in the capacity of the virus to infect (including transduction), or grow or replicate in a cell, to spread within one or more tissues, to produce a virus-encoded transgene from a cell, to lead to death of the infected cell or its neighbouring uninfected cells directly from a virally encoded component or indirectly through an immune response. By viral enhancement, it is also meant that the treatment leads to an increase in the yield of virus produced from a cell, either by increasing the virus' intrinsic capacity to infect, replicate, or spread, or its capacity to be produced with the help of additional components provided in trans (e.g. transfected plasmids).

In yet another embodiment of any of compositions, method or methods described above, the FMAE-containing compound enhances or increases interferon-sensitive oncolytic virus infection, growth or spread in cancer cells and tumors in vivo without inducing virus spread to major organs.

In a further embodiment of any of compositions, method or methods described above, the FMAE-containing compound enhances or increases virally induced cancer cell death in vivo and in vitro.

In still a further embodiment, which is not meant to be limiting, there is provided compositions comprising one or more of the FMAE-containing compounds, and one or more of a) an interferon-sensitive virus, a genetically modified interferon-sensitive virus, an attenuated interferon-sensitive virus, an oncolytic interferon-sensitive virus, an interferon-sensitive virus-based vaccine or gene therapy vector b) one or more cancer cells, c) a carrier, diluent or excipient, d) a pharmaceutically acceptable carrier, diluent or excipient, e) non-cancer cells; f) cell culture media; g) one or more cancer therapeutics; or any combination of a)-g). The present invention also contemplates embodiments wherein any one or a combination of a-g) are specifically excluded from the composition or kit. Any component or group of components may be excluded if desired.

In yet another embodiment, there is provided herein a kit comprising one or more of the FMAE-containing compounds, and one or more of a) an interferon-sensitive virus, a genetically modified interferon-sensitive virus, an attenuated interferon-sensitive virus, an oncolytic interferon-sensitive virus, an interferon-sensitive virus-based vaccine or gene therapy vector, b) one or more cancer cells, c) a pharmaceutically acceptable carrier, diluent or excipient, d) non-cancer cells; e) cell culture media; f) one or more cancer therapeutics, g) a cell culture plate or multi-well dish; h) an apparatus to deliver the compound to a cell, medium or to a subject; i) instructions for using the compound or any component in the kit, j) a carrier diluent or excipient, or any combination of a)-j). The present invention also contemplates kits wherein any one or a combination thereof of a)-j) are specifically excluded.

It will be understood by the person of skill in the art having regard to the teachings herein that enhancing or increasing viral activity, production, oncolytic activity, or cytotoxicity may include enhancing or increasing at least one of viral infection and/or rate thereof, viral production and/or rate thereof, viral titer and/or rate at which full titer may be reached, viral spread and/or rate thereof, cell lysis and/or rate thereof, viral cytotoxicity and/or rate thereof, or any combination thereof, as compared to when the one or more compounds are not used.

It will be understood by the person of skill in the art having regard to the teachings herein that enhancing or increasing the immunotherapeutic activity of an oncolytic virus may include enhancing or increasing the systemic antitumor immune response through the up-regulation of many cytokines, including higher expression of cytokines induced or expressed by the virus in presence of the FMAE-containing compounds.

As will be understood, in certain embodiments, FMAE-containing compounds, may include organic compounds which may be the cis or trans isomer of methyl or ethyl esters of maleic or fumaric acids. Mixtures of cis and trans isomers are also contemplated.

In certain embodiments, specific examples of a suitable Fumaric and Maleic Acid Ester (FMAE) compound may include:

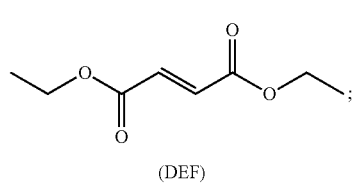

(DEF)

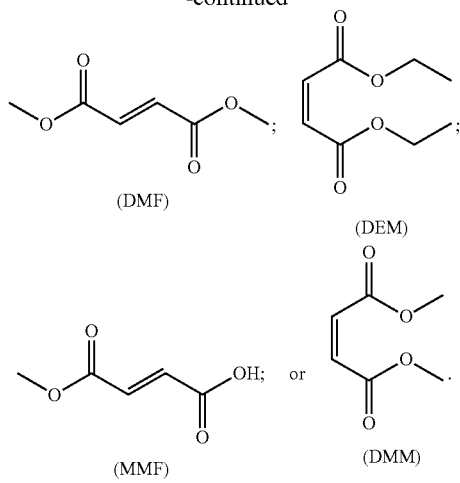

As will be understood, in certain embodiments, a Fumaric and Maleic Acid Ester (FMAE) compound may include any suitable fumaric or maleic acid derivative containing at least one ester moiety, and an α-β unsaturated carbon. In certain embodiments, FMAE compounds may include those of Formula (III) or Formula (IV):

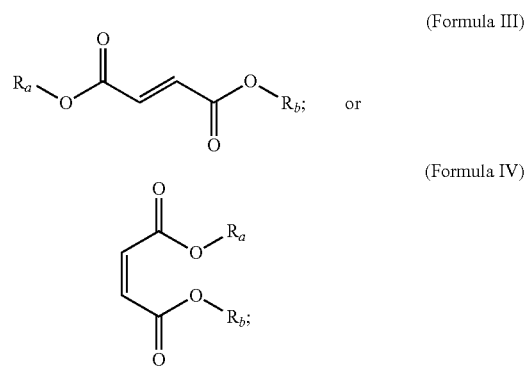

wherein $R_a$ and $R_b$ may be the same or different, and wherein at least one of $R_a$ and $R_b$ are selected to provide an ester functionality which is hydrolysable in vivo.

In certain embodiments, FMAE compounds may include those of Formula (III) or Formula (IV):

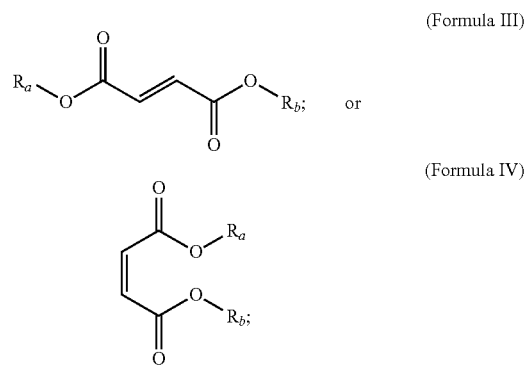

wherein $R_a$ and $R_b$ may be the same or different, and wherein $R_a$ and $R_b$ are each independently selected from:

hydrogen; a linear, branched, or cyclic saturated or unsaturated alkyl (such as a $C_1$-$C_{10}$ alkyl, for example), which may be optionally substituted (with, for example, one or more halogen, hydroxyl, nitro, or cyano); or may be absent (i.e. providing a carboxylate in Formula III or IV); and wherein when one of $R_a$ and $R_b$ is absent or is hydrogen, the other is present and is not hydrogen.

As will be understood, in certain embodiments, FMAE compounds may also include any suitable salt, ester, prodrug, functional mimic, precursor, or other suitable derivative of the FMAE compounds above.

Oncolytic viruses may include viruses that preferentially infect and lyse cancer or tumor cells as compared to non-cancer or normal cells, tumor cells including any cells that can form a tumor. Examples of oncolytic viruses known in the art include, without limitation, reovirus, newcastle disease virus, adenovirus, herpes virus, polio virus, mumps virus, measles virus, influenza virus, vaccinia virus, rhabdoviruses such as vesicular stomatitis virus and derivatives/variants thereof. In a preferred embodiment, the virus in the presence of an FMAE-containing compound, or derivative thereof, as described herein preferentially infects and lyses cancer cells or tumor cells as compared to the virus alone and as compared to normal cells alone or in the presence of the FMAE-containing compound or derivative.

It is contemplated that an interferon-sensitive virus may be any suitable virus known in the art which is interferon-sensitive or which is rendered interferon-sensitive, examples including, without limitation, replicating or non-replicating viruses such as: newcastle disease virus, polio virus, mumps virus, measles virus, influenza virus, Maraba virus (such as MG-1), Rabies virus, Rotavirus, Hepatitis A virus, Rubella virus, Dengue virus, Chikungunya virus, Respiratory Syncitial Virus, LCMV, lentivirus, replicating retrovirus, adenovirus, herpes simplex virus or rhabdovirus, or a variant or derivative thereof. In a preferred embodiment, the virus in the presence of an FMAE-containing compound, or derivative thereof, as described herein.

In certain embodiments, interferon-sensitive viruses may include viruses for which viral replication is controlled or inhibited by the action of antiviral type I or type III interferon in normal or interferon-responsive cancer cells.

Figure 5:
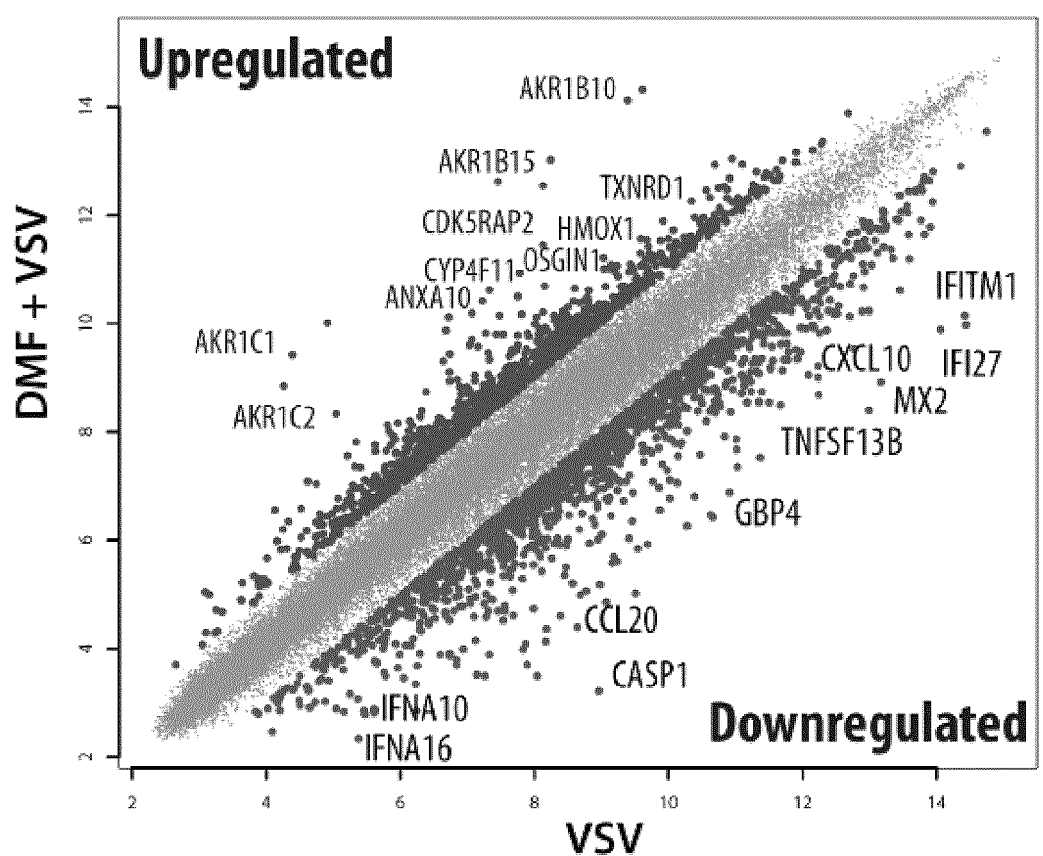
FIG. 5 shows that fumaric and maleic acid esters inhibited antiviral cytokine production and response to type I interferon. (A-E) Cell lysates of 786-0 treated with FMAEs and infected with VSVΔ51 expressing GFP were collected at 24 hpi and RNA or protein was extracted. (A) Scatter plot showing the expression levels of the differentially expressed genes between infected 786-0 in presence or absence of DMF. (B) Summary of gene ontology relationships and (C) list of top downregulated GOterm, by FMAEs during viral infection, and (D) heatmap showing the expression levels of the differentially expressed "response to virus" GOterm genes. (E) Protein was extracted and probed for indicated proteins by western blot. (F) 786-0 cells were pretreated for 4 hours with DMF or mock treated and infected with VSVΔ51 or wtVSV (MOI: 0.01). Corresponding viral titers were determined 48 hours post infection from supernatants (N=3; Error bars indicate SD). (G) 786-0 cells were treated with DMF, MMF, or mock treated for 4 hours and infected with VSVΔ51ΔG at MOI 1. 12 or 16 hpi supernatants were collected and used to precondition 786-0 cells for 4 hours and subsequently infected with VSVΔ51 or wtVSV. Corresponding viral titers were determined 48 hours post infection from supernatants (N=3; Error bars indicate SD). (H-I) 7860 were treated as in (A), (H) 16 hpi supernatant was collect and was subsequently assayed by Elisa for IFNβ (N=3; Error bars indicate SD). (I) 36 hpi supernatant was collect and was subsequently assayed by Elisa for IFNα (N=3; Error bars indicate SD). (J) 786-0 cells were treated with FMAEs for 6 h, and with IFNβ or IFNα for 4 hours, and subsequently infected with VSVΔ51 at MOI 0.1. Corresponding viral titers were determined 48 hours post infection from supernatants (N=3; Error bars indicate SD). (K) 786-0 cells were pre-treated with 200 μM of DMF for 1 or 4 hours and treated with IFNβ (250 U/mL) for 30 minutes. Proteins were extracted, and subsequently probed for pSTAT1, STAT1 and Actin, by western blot.
Figure 5:
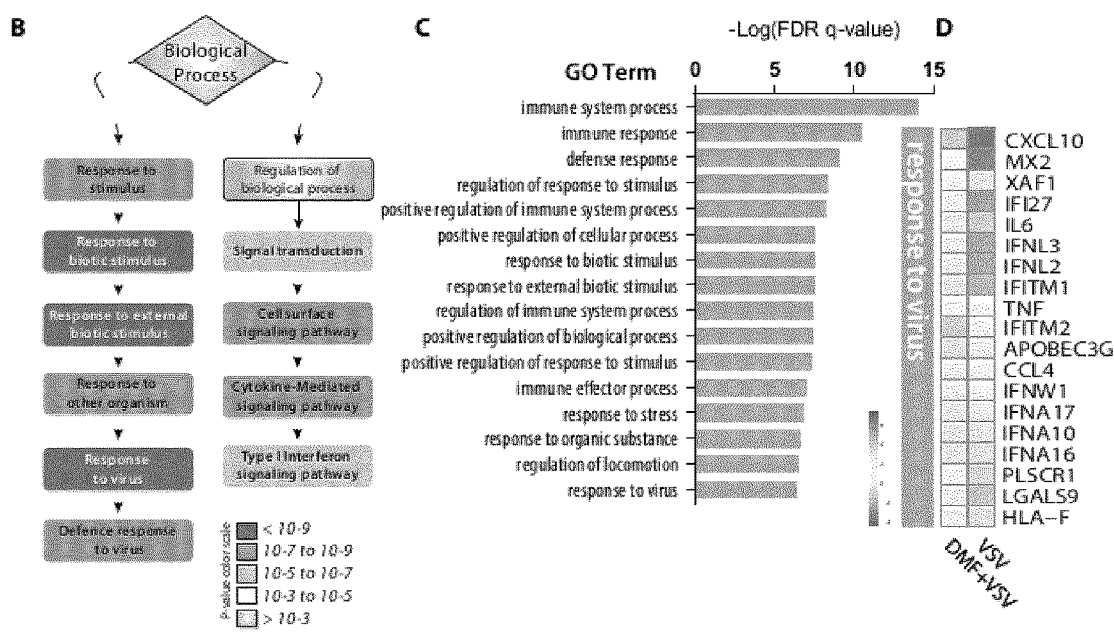
Figure 5:
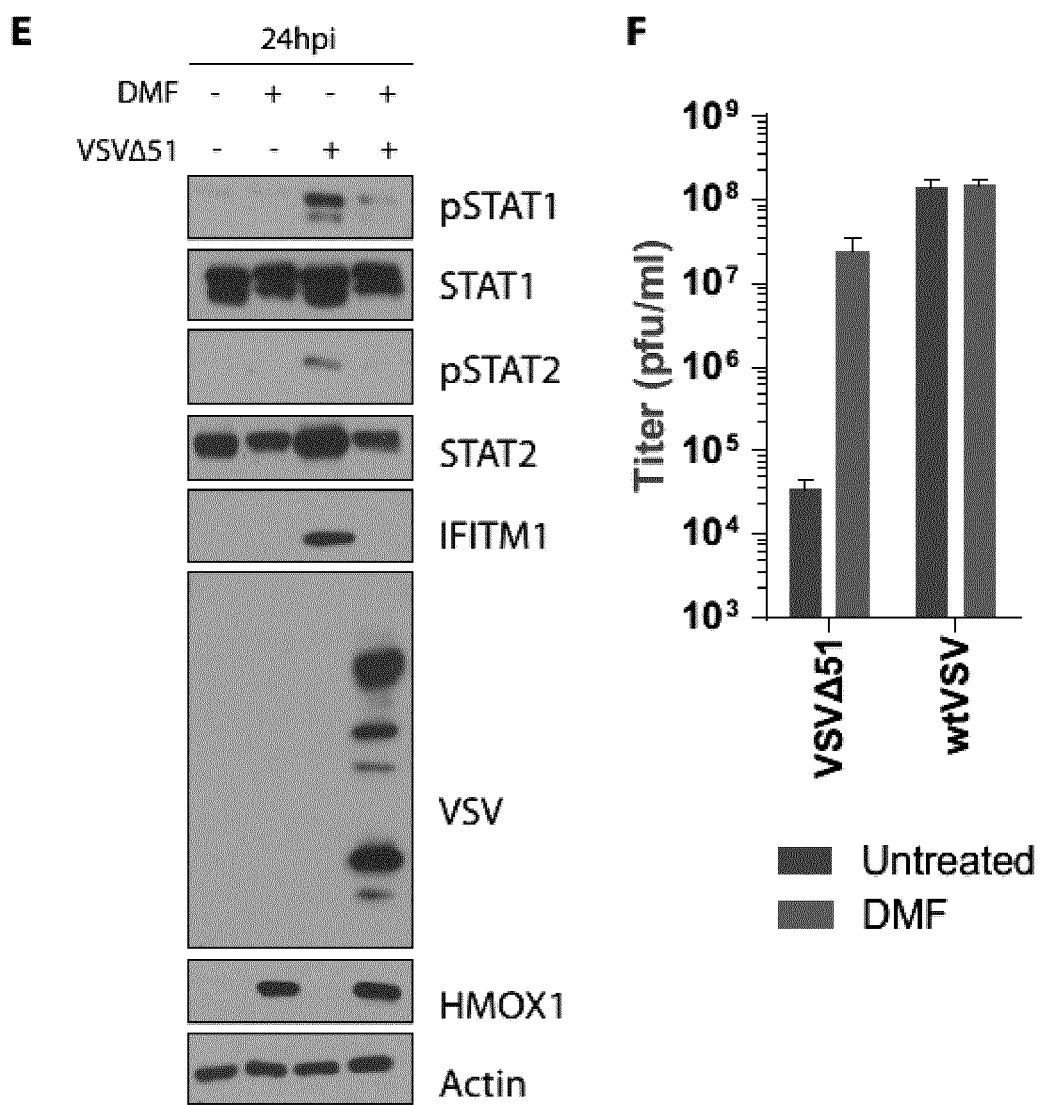
Figure 5:
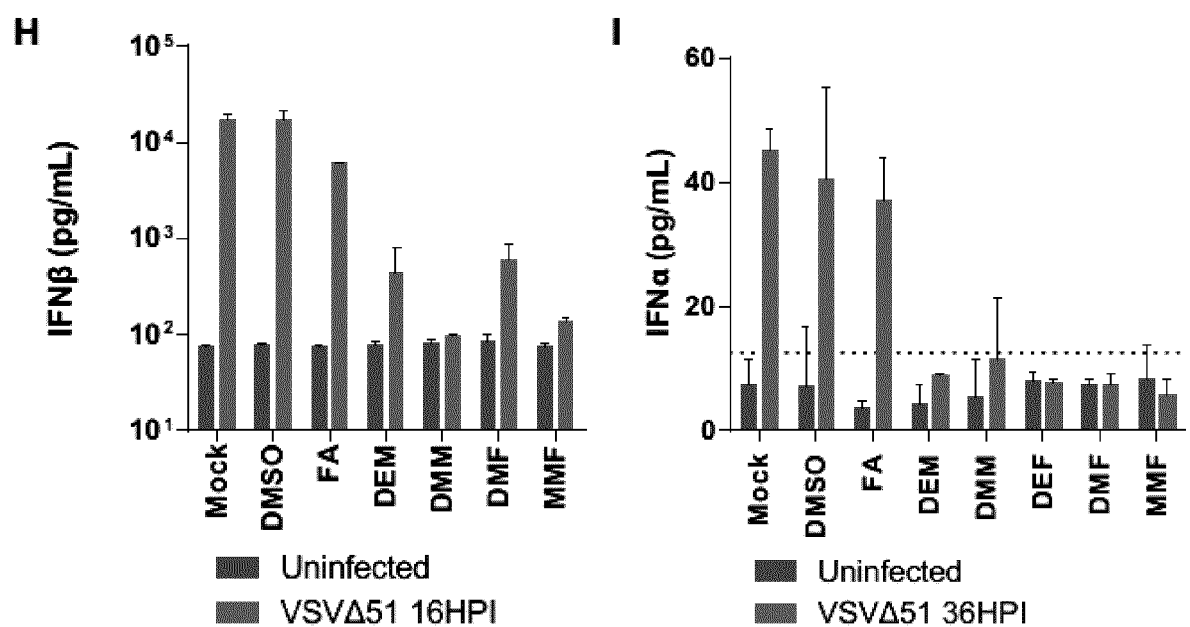
Figure 5:
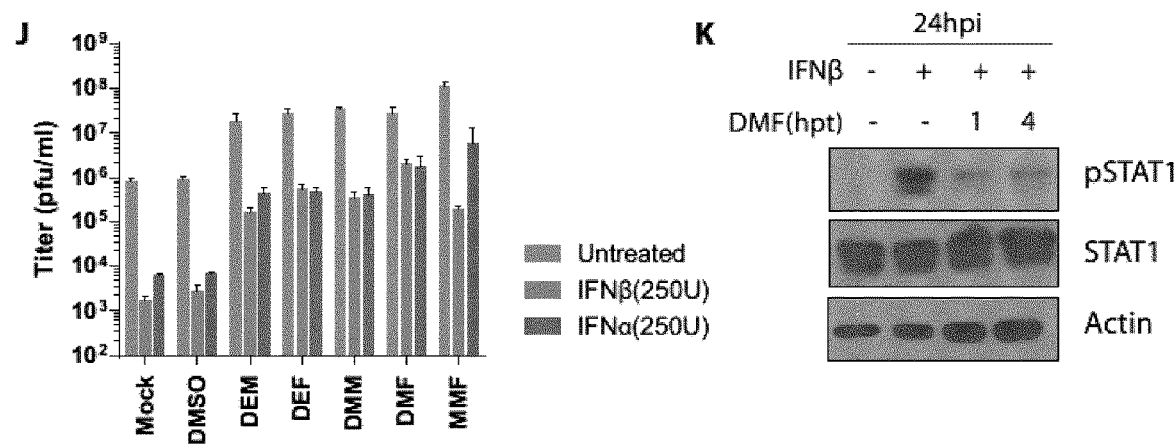

By interferon-sensitive, it is meant that following biologically relevant interferon treatment of cells that exhibit a normal capacity to respond to said interferon treatment and that are otherwise permissive to said virus, the virus, which can be either wild-type or its attenuated derivative strain rendered as such through genetic engineering and/or selection, experiences a reduction in its capacity to transduce, infect, replicate in, grow in, spread in, express transgene from, produce viral progeny from, or kill said cells. FIG. 5J provides an example of a means of testing interferon-sensitivity of a virus, where the live virus growth in the presence or absence of interferon in an infected cell determines the virus's interferon-sensitivity. For example, a virus that does not grow in cells pre-treated with any interferon, including but not limited to Type 1 IFN, but thrives in untreated cells would be considered interferon-sensitive. The viral growth decrease on interferon-sensitive cells following treatment with interferon may be of any detectable decrease, smaller decreases being associated with weaker effects, and larger decreases being associated with stronger effects.

Cytotoxic/oncolytic activity of the virus may be present, observed or demonstrated in vitro, in vivo, or both. In an embodiment, which is not meant to be limiting in any manner, the virus exhibits cytotoxic/oncolytic activity in vivo.

By a derivative or variant of a virus, it is meant a virus obtained by selecting the virus under different growth conditions, one that has been subjected to a range of selection pressures, that has been genetically modified using recombinant techniques known within the art, or one that has been engineered to be replication defective and/or express transgenes, or any combination thereof. Examples of such viruses are known in the art, for example from United States Patent Applications 20040115170, 20040170607, 20020037543, WO 00/62735; U.S. Pat. Nos. 7,052,832, 7,063,835, 7,122,182 (which are hereby incorporated by reference) and others. Preferably the virus is a Vesicular stomatitis virus (VSV), or a related rhabdovirus variant/derivative thereof, for example, selected under specific growth conditions, one that has been subjected to a range of selection pressures, one that has been genetically modified using recombinant techniques known within the art, or a combination thereof. In a preferred embodiment, the virus is VSVΔ51 [30].

The one or more types of cancer or tumor cells may be cancer or tumor or tumor-forming cells in vitro or in vivo from any cell, cell line, tissue or organism, for example, but not limited to human, rat, mouse, cat, dog, pig, primate, horse and the like, for example but not limited to tumor-forming cells such as 293-T cells, BHK21 cells, or MDCK cells. In a preferred embodiment, the one or more cancer or tumor cells comprise human cancer or tumor cells, for example, but not limited to lymphoblastic leukemia, myeloid leukemia, adrenocortical carcinoma, AIDS-related cancers, AIDS-related lymphoma, anal cancer, appendix cancer, astrocytoma, atypical teratoid/rhabdoid tumor, basal cell carcinoma, bile duct cancer, bladder cancer, bone cancer, osteosarcoma, malignant fibrous histiocytoma, brain stem glioma, brain tumor, cerebellar astrocytoma, cerebral astrocytoma/malignant glioma, craniopharyngioma, ependymoblastoma, medulloblastoma, pineal parenchymal tumors of intermediate differentiation, supratentorial primitive neuroectodermal tumors and pineoblastoma, visual pathway and hypothalamic glioma, spinal cord tumors, breast cancer, bronchial tumors, Burkitt lymphoma, carcinoid tumor, central nervous system lymphoma, cervical cancer, chordoma, chronic lymphocytic leukemia, chronic myelogenous leukemia, chronic myeloproliferative disorders, colon cancer, cutaneous T-Cell lymphoma, embryonal tumors, endometrial cancer, ependymoblastoma, ependymoma, esophageal cancer, extracranial germ cell tumor, extragonadal germ cell tumor, extrahepatic bile duct cancer, eye cancer, intraocular melanoma, retinoblastoma, gallbladder cancer, gastric (stomach) cancer, gastrointestinal carcinoid tumor, gastrointestinal stromal tumor (GIST), gastrointestinal stromal cell tumor, germ cell tumors, extracranial, extragonadal, ovarian, gestational trophoblastic tumor, glioma, hairy cell leukemia, head and neck cancer, hepatocellular (Liver) cancer, histiocytosis, Langerhans cell cancer, Hodgkin lymphoma, hypopharyngeal cancer, islet cell tumors, Kaposi sarcoma, kidney cancer, laryngeal cancer, lymphocytic leukemia, hairy cell leukemia, lip and oral cavity cancer, liver cancer, non-small cell lung cancer, small cell lung cancer, Hodgkin lymphoma, non-Hodgkin lymphoma, malignant fibrous histiocytoma of bone and osteosarcoma, medulloblastoma, medulloepithelioma, melanoma, intraocular melanoma, Merkel cell carcinoma, mesothelioma, metastatic squamous neck cancer, mouth cancer, multiple endocrine neoplasia syndrome, multiple myeloma/plasma cell neoplasm, nasal cavity and paranasal sinus cancer, nasopharyngeal cancer, neuroblastoma, oral cancer, oropharyngeal cancer, ovarian cancer, pancreatic cancer, parathyroid cancer, penile cancer, pharyngeal cancer, pheochromocytoma, pineal parenchymal tumors, pineoblastoma and supratentorial primitive neuroectodermal tumors, pituitary tumor, plasma cell neoplasm/multiple myeloma, pleuropulmonary blastoma, primary central nervous system lymphoma, prostate cancer, rectal cancer, renal cell (kidney) cancer, renal pelvis and ureter cancer, transitional cell cancer, respiratory tract carcinoma, retinoblastoma, rhabdomyosarcoma, salivary gland cancer, uterine sarcoma, skin cancer, Merkel cell skin carcinoma, small intestine cancer, soft tissue sarcoma, squamous cell carcinoma, squamous neck cancer, stomach (Gastric) cancer, supratentorial primitive neuroectodermal tumors, T-Cell lymphoma, testicular cancer, throat cancer, thymoma and thymic carcinoma, thyroid cancer, trophoblastic tumor, urethral cancer, uterine cancer, endometrial cancer, uterine sarcoma, vaginal cancer, vulvar cancer, or Wilms tumor. However, the compounds and compositions described herein possible may be used to treat other cancers or tumor in vivo or in vitro.

For in vivo therapeutic applications, preferably there is provided a pharmaceutical composition comprising one or more FMAE-containing compounds and a pharmaceutically acceptable carrier, diluent or excipient, optionally containing other solutes such as dissolved salts and the like. In a preferred embodiment, the solution comprises enough saline, glucose or the like to make the solution isotonic. Pharmaceutical compositions and methods of preparing pharmaceutical compositions are known in the art and are described, for example, in "Remington: The Science and Practice of Pharmacy" (formerly "Remingtons Pharmaceutical Sciences"); Gennaro, A., Lippincott, Williams & Wilkins, Philadelphia, PA (2000), herein incorporated by reference.

Administration of such compositions may be via any number of routes depending upon whether local and/or systemic treatment is desired and upon the area to be treated. In a first embodiment, which is not meant to be limiting, the compound is administered locally to the area to be treated. Administration may be topical (including ophthalmic and to mucous membranes including vaginal and rectal delivery), pulmonary (e.g. by inhalation or insufflation of powders or aerosols, including by nebulizer), intratracheal, intranasal, epidermal and transdermal, oral or parenteral. Parenteral administration includes intravenous, intraarterial, subcutaneous, intraperitoneal or intramuscular injection or infusion, or intracranial, e.g. intrathecal or intraventricular, administration. Also contemplated is intra-tumor injection, perfusion or delivery into the general vicinity of the tumor or injection into the vasculature supplying a tumor. Alternatively, the FMAE-containing compounds may be formulated in a tablet or capsule for oral administration. Alternate dosage forms, including slow-release, sustained-release, extended release, as would be known in the art are also contemplated.

For administration by inhalation or insufflation, the compounds can be formulated into an aqueous or partially aqueous solution, which can then be utilized in the form of an aerosol. For topical use, the modulators can be formulated as dusting powders, creams or lotions in pharmaceutically acceptable vehicles, which are applied to affected portions of the skin.

Without wishing to be limiting, the dosage requirements for the FMAE-containing compounds of the present invention may vary with the particular compositions employed, the route of administration and the particular subject being treated. Dosage requirements can be determined by standard clinical techniques known to a worker skilled in the art. Typically, treatment will be generally initiated with small dosages less than the optimum dose of the compound or compound/virus. Thereafter, the dosage is increased until the optimum or satisfactory effect under the circumstances is reached. In general, the FMAE-containing compound or pharmaceutical compositions comprising the FMAE-containing compound are administered at a concentration that will generally afford effective results without causing significant harmful or deleterious side effects. Administration can be either as a single unit dose or, if desired, the dosage can be divided into convenient subunits that are administered at suitable times throughout the day.

The FMAE-containing compound may be employed in sequential administration, for example, before, after or both before and after administration of an interferon-sensitive virus, for example, but not limited to an attenuated virus, a genetically modified virus, a vaccine virus, a gene therapy vector or an oncolytic virus. Alternatively, the FMAE-containing compound may be administered concurrently or in combination with a virus as described above, for example in combination with an oncolytic virus. In addition, the FMAE-containing compound may be used with an oncolytic virus as described above and in combination with one or more cancer therapeutics or cancer therapies as is known to a person of skill in the art, for example but not limited to interferon therapy, interleukin therapy, colony stimulating factor therapy, immunotherapy, immune checkpoint inhibitor therapy, chemotherapeutic drugs, for example, but not limited to 5-fluorodeoxyuridine amsacrine, bleomycin, busulfan, capecitabine, carboplatin, carmustine, chlorambucil, cisplatin, cladribine, clofarabine, crisantaspase, cyclophosphamide, cytarabine, dacarbazine, dactinomycin, daunorubicin, docetaxel, doxorubicin, epirubicin, etoposide, fludarabine, fluorouracil, gemcitabine, gliadel, hydroxycarbamide, idarubicin, ifosfamide, irinotecan, leucovorin, lomustine, melphalan, mercaptopurine, mesna, methotrexate, mitomycin, mitoxantrone, oxaliplatin, paclitaxel, pemetrexed, pentostatin, procarbazine, raltitrexed, satraplatin, streptozocin, tegafur-uracil, temozolomide, teniposide, thiotepa, tioguanine, topotecan, treosulfan, vinblastine, vincristine, vindesine, vinorelbine or a combination thereof. Further, anti-cancer biologics may also be employed, for example, but without limitation, monoclonal antibodies and the like.

The present invention also contemplates methods and uses of the compositions as described herein for increasing or enhancing the spread of an interferon-sensitive virus, for example, a genetically modified virus, an attenuated virus, a vaccine virus, a gene therapy vector, or an oncolytic virus in one or more cells, for example, but not limited to one or more types of immortalized, cancer or tumor cells, increasing or enhancing the cytotoxicity/oncolytic activity of an oncolytic virus against one or more cancer or tumor cells, increasing or enhancing the production, yield or reproductive capacity of a virus, for example, a genetically modified virus, an attenuated virus, a vaccine virus, a gene therapy vector, an oncolytic virus, or, any combination of the above. In an embodiment, which is not meant to be limiting in any manner, the compositions reduces the viability of a cancer or tumor cell by either killing the cancer or tumor cell or limiting its growth for a period of time.

In another embodiment, the cells may be cancer cells in vivo, or in vitro. In a further embodiment, the in vivo cancer cells may be from a mammalian subject. In still a further embodiment, the mammalian subject may be a human subject. In another embodiment the cells are immortalized cells in vitro.

The present invention also contemplates methods and uses of the compositions as described herein for increasing or enhancing the production, infection, growth and spread of an interferon-sensitive virus, for example, a genetically modified virus, an attenuated virus, a vaccine virus, a gene therapy vector, or an oncolytic virus in one or more cells, for example, but not limited to one or more types of immortalized, cancer or tumor cells, increasing or enhancing the production, yield or reproductive capacity of a virus, for example, a genetically modified virus, an attenuated virus, a vaccine virus, a gene therapy vector, an oncolytic virus, or, any combination of the above.

In the following examples, DMF and various fumaric and maleic acid esters (FMAEs) were observed as enhancing viral infection of several oncolytic viruses (OV) in cancer cell lines as well as in human tumor biopsies, improving therapeutic outcomes in resistant syngeneic and xenograft tumor models. Durable responses, including enhanced spread and oncolysis, were observed, even in example models otherwise refractory to OV and drug monotherapies. Without wishing to be bound by theory, the observed ability of DMF to enhance viral spread may be due to its ability to inhibit type I IFN production and response, which may be associated with its ability to block nuclear translocation of transcription factor NF-kB, thereby providing assistance in overcoming innate cancer cell immune response. In certain non-limiting embodiments of the experimental results, FMAEs improved viral spread/growth in tumor cells as compared with virus growth in normal tissues, which may be advantageous in targeting cancer, for example. In the following studies, FMAE treatment was observed as reducing innate immune response to infection with oncolytic virus, thereby enhancing viral efficacy.

Figure 3:
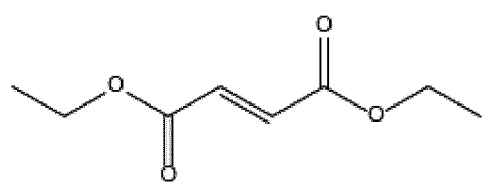
FIG. 3 shows that various fumaric and maleic acid esters promoted infection of oncolytic virus VSVΔ51. (A) Structure of fumaric acid esters (DEF, DMF) and maleic acid esters (DEM, DMM) are presented. (B) Metabolism of DMF. DMF is hydrolyzed into monomethyl fumarate (MMF), which in turn is metabolized into fumaric acid (FA). FA subsequently enters the TCA cycle. (C) 786-0 cells or (D) CT26WT ex vivo tumor cores were pretreated with various FMAEs and analogues for 4 hours and subsequently infected with oncolytic VSVΔ51 expressing GFP at (C) an MOI of 0.01 or (D) $1 \times 10^4$ PFU. 24 hours post infection fluorescent images were taken of the infected 786-0 cells or CT26WT tumor cores. Corresponding viral titer were determined 48 hours post infection from supernatants. (N=3; Error bars indicate SD; one-way ANOVA; * p<0.05,  p<0.01, * p<0.001, as compared to the untreated counterpart). (E) 786-0 cells and CT26WT cells were treated with various FMAEs, at indicated concentrations, for 4 hours and subsequently infected with VSVΔ51 (MOI: 0.01), supernatants were collected 48 hours post infection, and titered by plaque assay. (N=3; Error bars indicate SD). (F) 786-0 were pretreated for 4 hours with various FMAEs and were subsequently infected with VSVΔ51 expressing GFP, an agarose overlay was added after 1 hour of infection. Fluorescence microscopy of a representative plaque 24 hour after infection. Corresponding image of Coomassie blue stain of the full well and average plaque diameter illustrating the enhancement of the plaque diameters in presence of DMF (N=20; Bars indicate mean; 1 way ANOVA; *** p<0.001, as compared to the mock condition counterpart).
Figure 3:
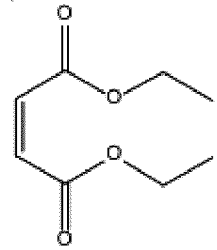
Figure 3:
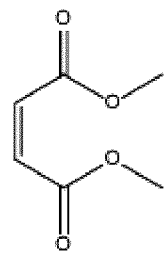
Figure 3:
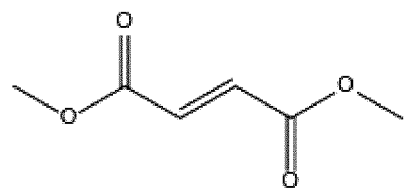
Figure 3:
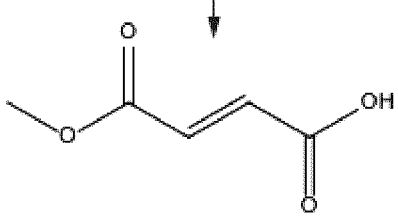
Figure 3:
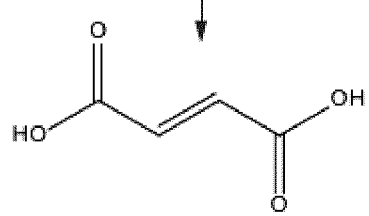
Figure 3:
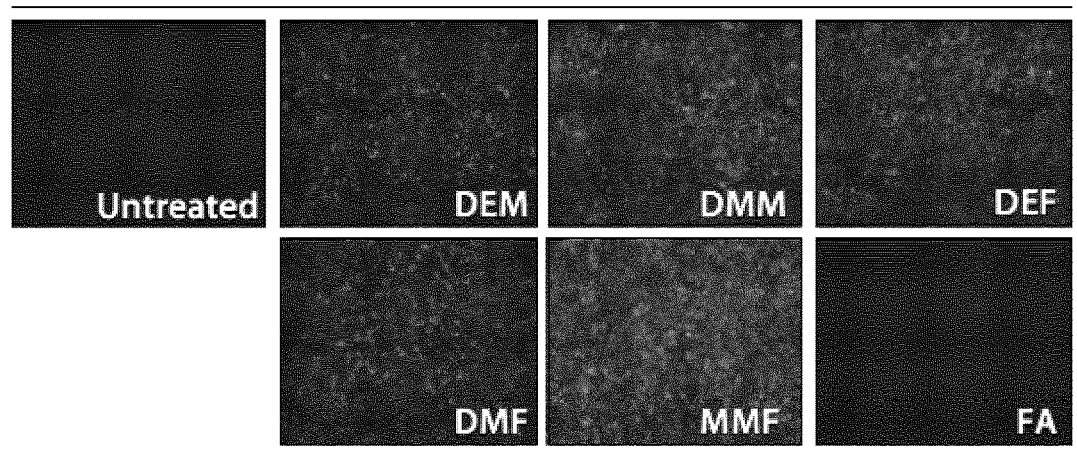
Figure 3:
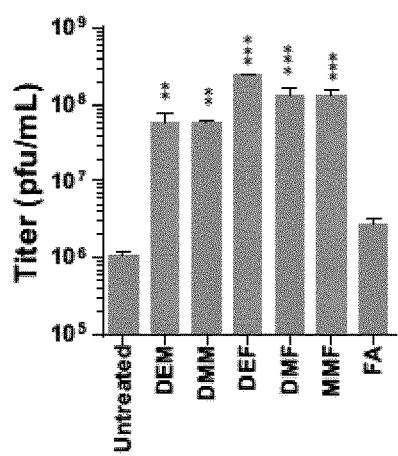
Figure 3:
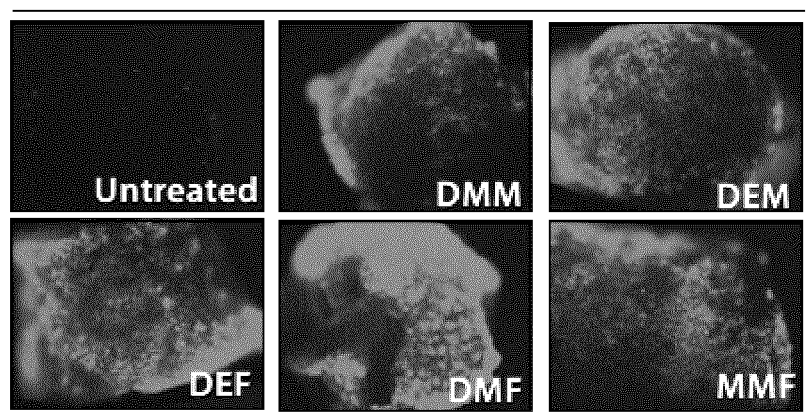
Figure 3:
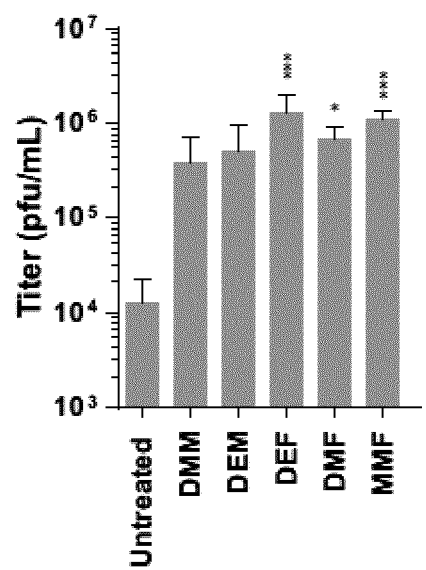
Figure 3:
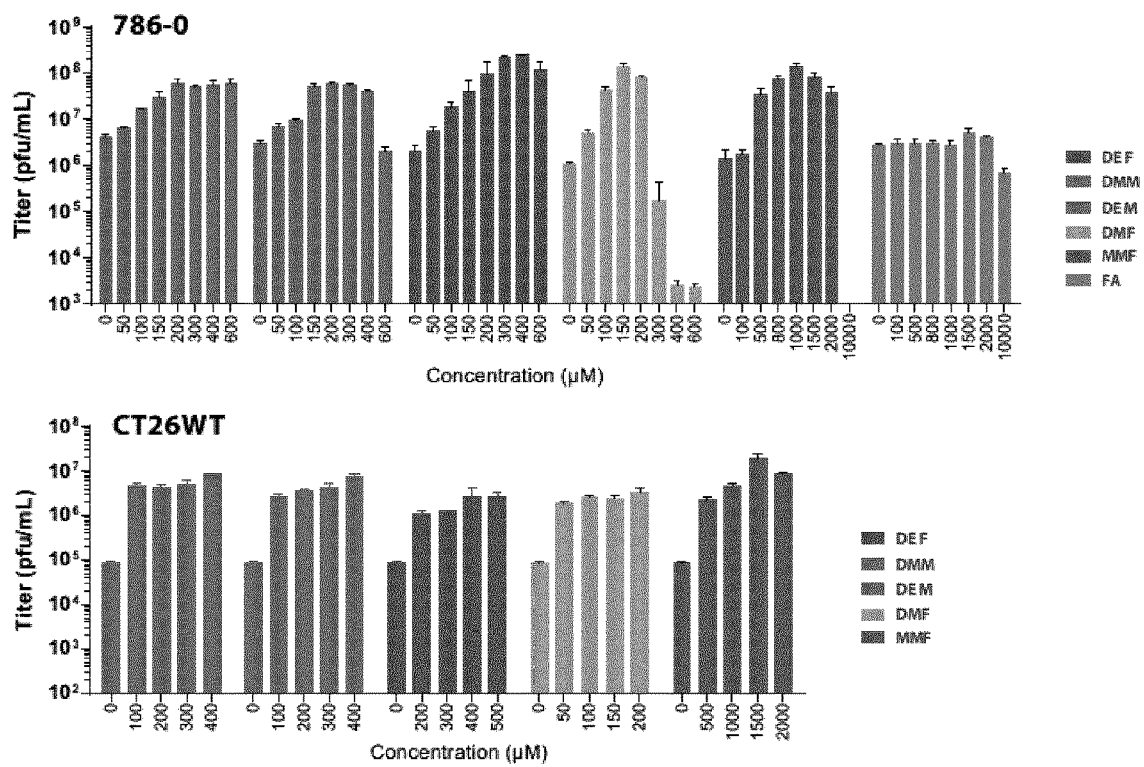
Figure 3:
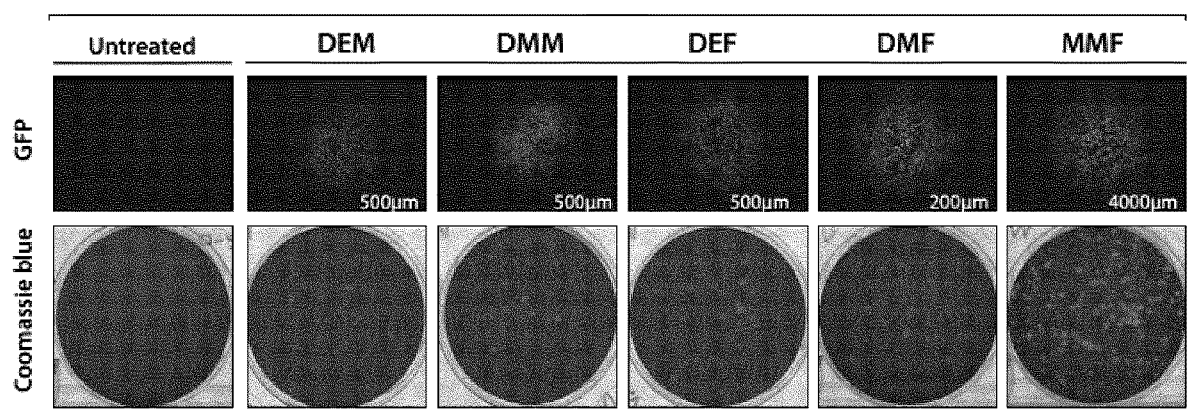
Figure 3:
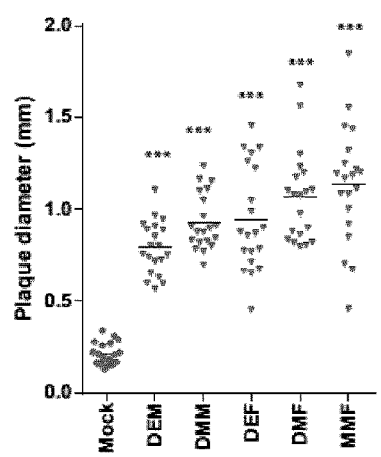

Additional examples show that DMF and various fumaric and maleic acid esters (FMAEs) including MMF can increase or enhance the production, yield or reproductive capacity of viruses in immortalized non-cancer cells. In one embodiment, DMF treatment was found to enhance the productivity of attenuated replication competent interferon-sensitive Influenza A H1N1 FM/1/47 virus in immortalized non-cancerous Vero African green monkey kidney cells. In another embodiment, MMF was observed to enhance the production of a replication defective lentivirus following transfection of 293T cells with plasmids encoding viral packaging proteins.

The present invention will be further illustrated in the following examples.

EXAMPLES

Example 1 Dimethylfumarate Enhances Tumor-Specific Viral Spread and Oncolysis In Vitro We first examined the impact of DMF (structure displayed in FIG. 1A) on the growth of oncolytic vesicular stomatitis virus (VSVΔ51). Notably, VSV and closely related Maraba are currently undergoing clinical evaluation but face resistance to infection in approximately a third of cancers [30-31]. 786-0 renal carcinoma cells are highly refractory to VSVΔ51 infection, however a 4-hour pre-treatment with DMF at doses between 50 and 200 μm, increased VSVΔ51 virus growth at a low multiplicity of infection (MOI) by more than 100-fold (FIG. 1C). Virus-encoded GFP expression was also greatly enhanced as visualized by microscopy (FIG. 1B). This effect was observed with pre-treatment times up to 24 hours prior to infection, and post-infection up to 8 hours (FIG. 1K). More broadly, DMF robustly enhanced infection in a panel of human and murine cancer cell lines (sarcoma, osteosarcoma, breast, colon, melanoma, ovarian) with a wide range of sensitivity to VSVΔ51 (FIG. 1D). DMF also improved viral output of oncolytic herpes virus (HSV-1 mutant N212) and Sindbis virus following treatment in 786-0 cells (FIGS. 1, E and F). Furthermore, we also tested the effect of DMF on adenoviruses, which in addition to oncolytic virotherapy have been extensively used as gene therapy vectors [32]. Pretreatment of human lung adenocarcinoma A549 cells with DMF increased luciferase transgene expression of non-replicating adenovirus, E1A-deleted Ad5 over the course of 7 days by up to 20-fold (FIG. 1G). Single and multi-step growth curves performed in 786-0 cells revealed that DMF enhanced the viral output of VSVΔ51 when using a low MOI, but not when using a high MOI (FIG. 1H), indicating DMF inhibits mechanisms that impinge on viral spread rather than virus output per infected cell. To further explore the effect of DMF on virus spreading, 786-0 cell monolayers were infected with VSVΔ51 and overlaid with agarose to generate defined plaques of virus replication foci. DMF substantially increased the average plaque diameter of VSVΔ51 on fluorescent imaging and Coomassie Blue staining of infected cell monolayers (FIG. 1I). To further assess the oncolytic effect of VSVΔ51 in the presence of DMF, we pretreated cancer cells with DMF prior to infection with a low MOI of VSVΔ51, and cell viability was assessed with the metabolic dye alamarBlue®, 48 hours post-infection. Combined treatment with DMF and VSVΔ51 led to what appears to be a synergistic decrease in cell viability in human 786-0 as well murine CT26WT and B16F10 cells (FIG. 1J).

Example 2 Dimethyl Fumarate Enhances Tumor-Specific Infection Ex Vivo and in Human Clinical Samples We further assessed the ability of DMF to enhance VSVΔ51 infection ex vivo in mouse-derived tissues. Tumor cores from mice subcutaneously implanted with CT26WT murine colon cancer cells or B16F10 murine melanoma cancer cells, as well as cores from normal lung, muscle, and spleen were collected and subsequently infected with VSVΔ51-GFP in the presence or absence of 150 μM DMF. DMF robustly increased the growth of the virus in tumor CT26WT and B16F10 cores by 31-fold and 13-fold, respectively, but did not increase virus growth in normal tissue cores (FIGS. 2, A and B). Furthermore, DMF increased VSVΔ51 infection by >10-fold ex vivo in primary human melanoma, lung, prostate and ovarian tumor samples as observed by plaque assay and microscopy (FIGS. 2, C and D), as well as in various melanoma and ovarian patient-derived cancer cell lines (FIG. 2E). Similar to the murine normal tissue cores, DMF did not improve virus growth in human normal lung and muscle tissues from various patients (FIG. 2F).

Example 3

In addition to DMF, various fumaric and maleic acid esters (FMAEs) have been found to exhibit anti-inflammatory, and immunomodulatory properties [33]. We therefore tested whether other FAEs, and their cis- and trans-isoforms (maleic acid esters) (FIGS. 3, A and B) have a similar impact to DMF on viral infection of cancer cells. Indeed, cell-permeable FAE such as diethyl fumarate (DEF), and maleic acid esters dimethyl maleate (DMM) and diethyl maleate (DEM) robustly enhanced VSVΔ51 infection, spread, and oncolysis in 786-0 and CT26WT cells in vitro (FIG. 3C, E, F). Enhanced infection was also observed with FMAEs in CT26WT tumor cores infected ex vivo (FIG. 3D). DMF is rapidly hydrolyzed to monomethyl fumarate (MMF) by esterases in vivo, and subsequently to fumaric acid (FA) (as displayed in FIG. 3B) [34]. Indeed, MMF is thought to be the active metabolite of DMF in the treatment of multiple sclerosis [34]. In 786-0 cells MMF also substantially enhanced infection of VSVΔ51 to a similar extent as DMF, albeit at higher effective doses. Fumaric Acid (FA), in contrast with the cell-permeable esters MMF and DMF, had no impact on viral growth (FIG. 3C,E). Taken together, our data indicate that DMF and other cell-permeable FMAEs can dramatically enhance the spread of OVs in both mouse and human cell lines and cancer tissue explants.

Figure 4:
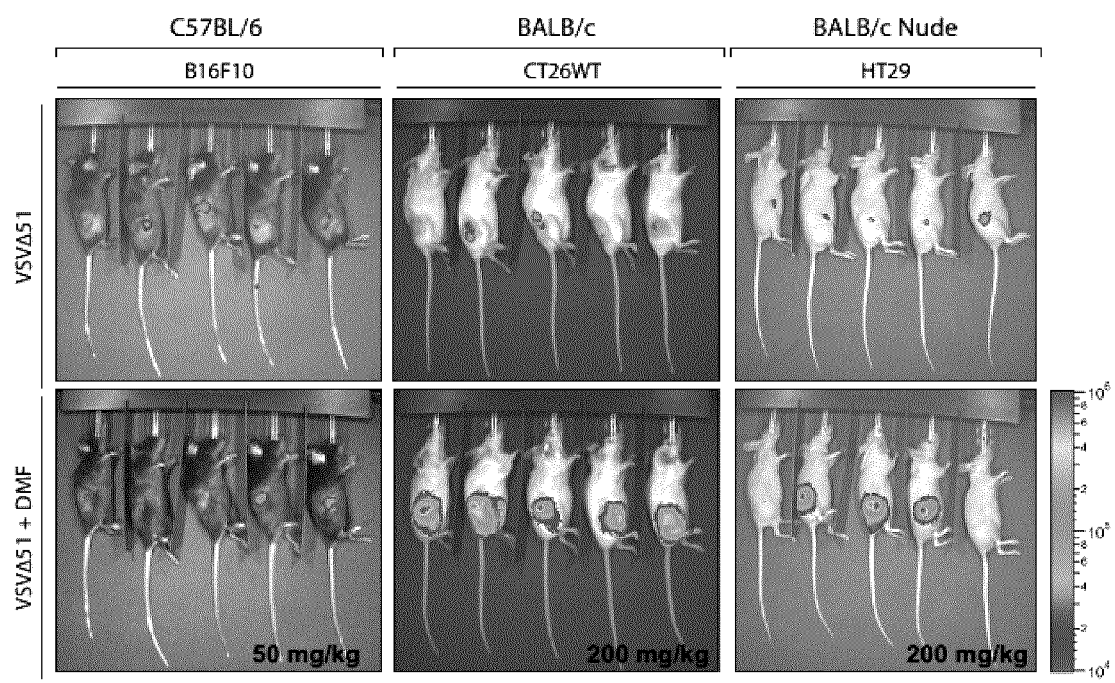
FIG. 4 shows that dimethyl fumarate enhanced VSVΔ51 therapeutic efficacy in syngeneic and xenograft tumor models. (A-C) CT26WT, B16F10 and HT29, tumor-bearing mice were treated intratumorally with the vehicle (DMSO) or 50 or 200 mg/kg (as indicated in A) of DMF for 4 hours, and subsequently injected with $1 \times 10^8$ PFU of oncolytic VSVΔ51 expressing firefly-luciferase or the vehicle (PBS), intratumorally. The treatment was administered twice or three times, as indicated by arrows in panel C. 24 hours post infection, viral replication was monitored. (A) Representative bioluminescence images of mice presented. (B) Quantification of luminescence. Scale represented in photons. (N=10-18. Bars indicates mean; ns, no statistical significance; **p<0.01 by 2-tailed t-test; as compared to VSVΔ51 infected condition). (C) Tumor volume graphed (N=9-15. Error bars indicate SEM; *p<0.05,  p<0.01, *p<0.001 by two-way ANOVA; as compared to DMF+VSVΔ51 to DMSO alone condition). (D) Survival was monitored over time. Log-rank (Mantel-Cox) test indicates that the combined treatment is significantly prolonged over VSVΔ51 alone (CT26WT N=10-13, p=0.0008; B16F10 N=9-14, p=0.0039; HT29 N=10-15, p=0.0003). (E) Tumor volume and survival was monitored after re-implantation of CT26WT in cured and naïve mice from D (N=3-5, Error bars indicate SD). (F) Tumor volume was monitored after implantation of 4T1 cells in CT26WT-cured and naïve mice (N=3, Error bars indicate SD).
Figure 4:
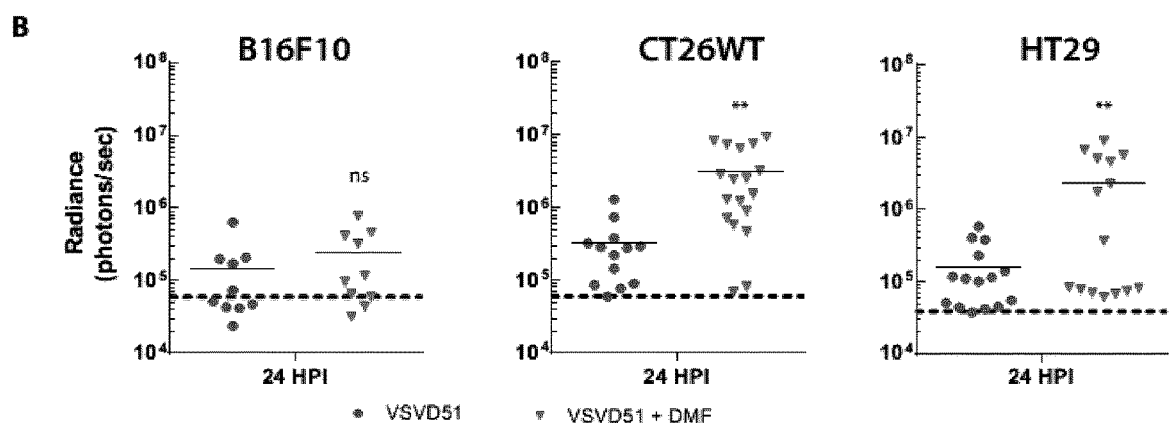
Figure 4:
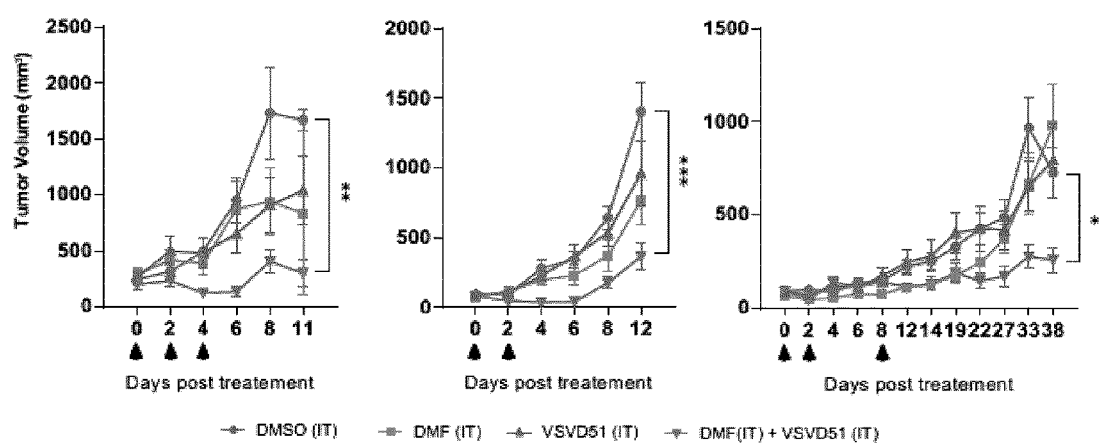
Figure 4:
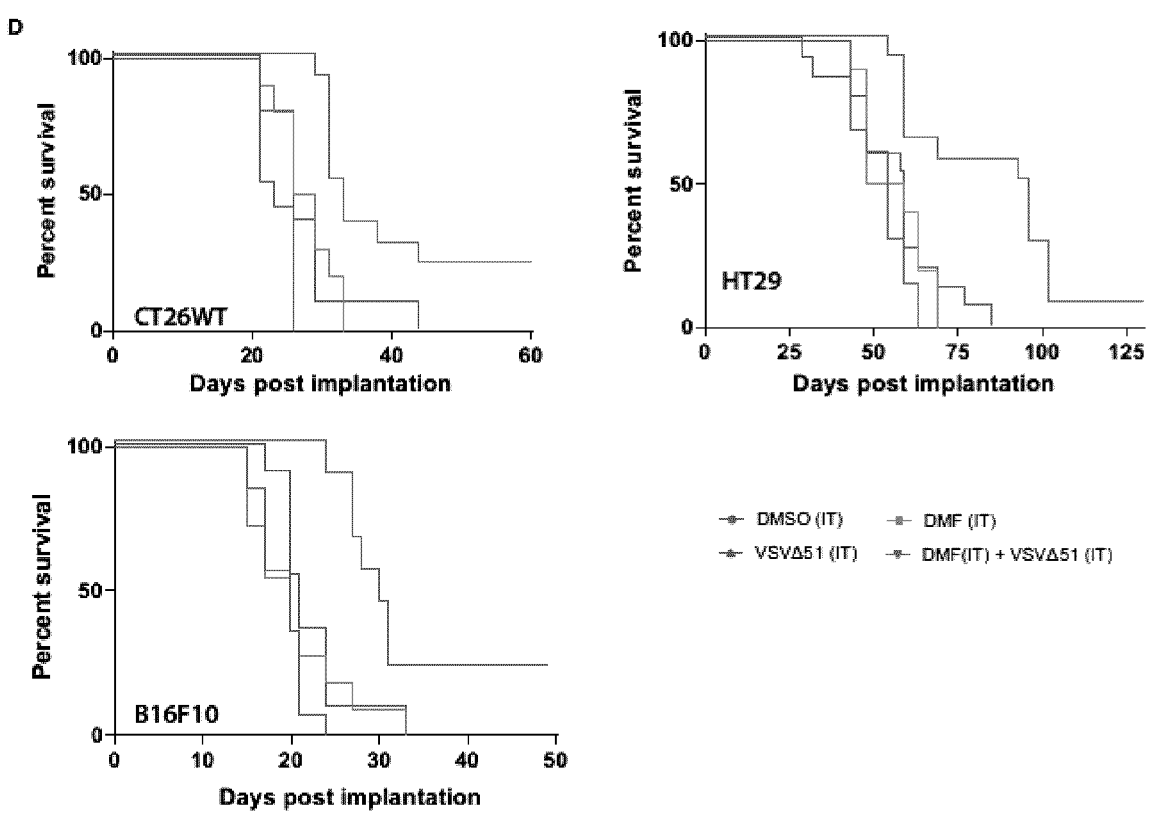
Figure 4:
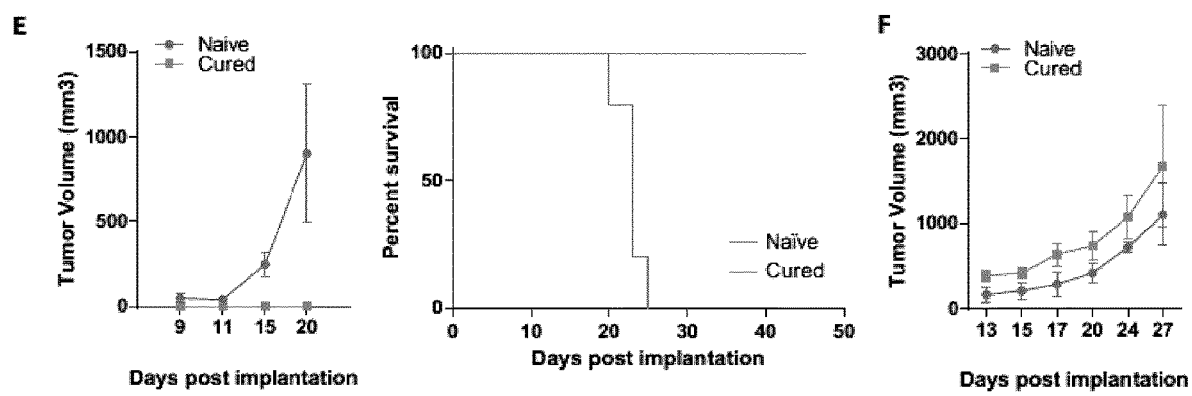

Example 4 Dimethyl Fumarate Improves Therapeutic Efficacy of Oncolytic Rhabdoviruses in Mouse Preclinical Models Since DMF is a clinically approved drug and since it broadly and robustly enhanced the growth and activity of VSVΔ51 in vitro in both human and mouse tumor explants in the studies described herein, and did so preferentially in tumors opposed to normal tissues, we next evaluated the potential therapeutic benefit of combining DMF with oncolytic VSVΔ51 in vivo. To this end, we used both syngeneic and xenograft mouse tumor models, in which we have previously shown VSVΔ51 to be ineffective as a monotherapy [35-38]. Mouse CT26WT, B16F10 and human colon cancer HT29 cells were grown subcutaneously in Balb/c, C57BL/6 or nude mice, respectively. Mice were injected intratumorally with DMF for 4 hours, and subsequently infected with VSVΔ51 expressing luciferase. With the exception of the B16F10 model, DMF enhanced virus-associated luciferase gene expression specifically in tumors 24 hours after the first injection of virus, as assessed using an in vivo imaging system (IVIS) (FIG. 4A, B). Nevertheless, in all three models, the combination therapy led to considerable delay in tumor progression (FIG. 4C), as well as significantly prolonged survival compared with either monotherapy (FIG. 4D). The combination therapy led to complete remission in approximately 20% of the mice in both the CT26WT and B16F10 models. The cured CT26WT-bearing mice that had received the combination regimen subsequently became immune to re-challenge with the same cancer cells (FIG. 4E). However, when cured CT26WT-bearing mice were challenged with a foreign tumor (murine 4T1 breast cancer), cured CT26WT mice grew 4T1 tumors at a similar rate as the naive mice (FIG. 3F). Altogether indicating the effective generation of a specific and long-lasting anti-tumor immunity.

Example 5 Fumaric and Maleic Acid Esters Inhibit the Antiviral Response

To gain further insight into the possible mechanism mediating the enhancement of OVs by DMF and other FMAEs, microarray gene expression analysis was performed on 786-0 cells 24 hours following infection with VSVΔ51 in the presence or absence of DMF, DEM, DEF, DMM. Upon infection with VSVΔ51, multiple antiviral genes were up-regulated as expected; however, DMF led to the inhibition of many of these (ifitim1, mx2, gbp4, ifi27, ifna, cxcl10), and upregulated various gene, including a number of redox response genes (cyp4f11, cdk5rap2, anxa10 hmox1, osgin1, txnrd1, akr1b10, akr1b15, akr1c1, akr1c2) (FIG. 5A, D). GOterm analysis revealed that FMAEs treatment of infected 786-0 cells led to the inhibition of the response to virus as well as type I IFN signaling (FIGS. 5B, C and D). Consistent with repression of the type I IFN response, DMF decreased activation (phosphorylation) of both STAT1 and STAT2, 24 hours post infection (FIG. 5E). Additionally, expression levels of the antiviral protein IFITM1 was potently repressed by DMF, while VSV-viral proteins were increased (FIG. 5E). Furthermore, DMF enhanced infection of VSVΔ51, however had no impact on infection of 786-0 cells by wild-type VSV (wtVSV) (FIG. 5F). Unlike VSVΔ51, wtVSV is known to robustly inhibit Type I IFN production, and therefore the effect of DMF may be expected to be redundant in the context of wtVSV if a Type I IFN response is indeed involved in eliciting the pro-viral effects of DMF. To gain mechanistic insight into the effect of FMAEs on the antiviral response, we examined their ability to protect against virus challenge and IFN-mediated antiviral signaling. Following treatment with FMAEs (or mock), we infected cells with a spread-deficient version of VSVΔ51 that does not encode the viral G protein (glycoprotein responsible for virus budding, host cell binding, and virus entry; VSVΔ51ΔG) to suppress formation of de novo virions [39]. Cell supernatants were collected 12 or 16 hpi, and used to pretreat target cells prior to infection with VSVΔ51 or wtVSV. Our results show that while the supernatant of cells infected with VSVΔ51ΔG could protect against subsequent viral infection with VSVΔ51 or wtVSV, the addition of DMF or MMF was able to completely overcome this suppressive effect for both VSVΔ51 and wtVSV (FIG. 5G). Indeed, we observed through ELISA a decrease in the production of IFNβ and IFNα following infection in the presence of FMAEs (FIG. 5H, I). Furthermore, treatment of cells with DMF and other FMAEs antagonized the antiviral effects of Type I IFN pretreatment on VSVΔ51 infection (FIG. 5J). Taken together, these data suggest that FMAEs affect antiviral signaling, which represses production of Type I IFN and downstream signaling through the JAK-STAT pathway. Consistent with this, Western blotting experiments reveal that in cells conditioned with IFNβ at the doses which enhanced VSVΔ51 infection, DMF and DEM inhibited STAT1 phosphorylation, which is involved in transcription and response to type I IFN following viral infection (FIG. 5K).

Figure 6:
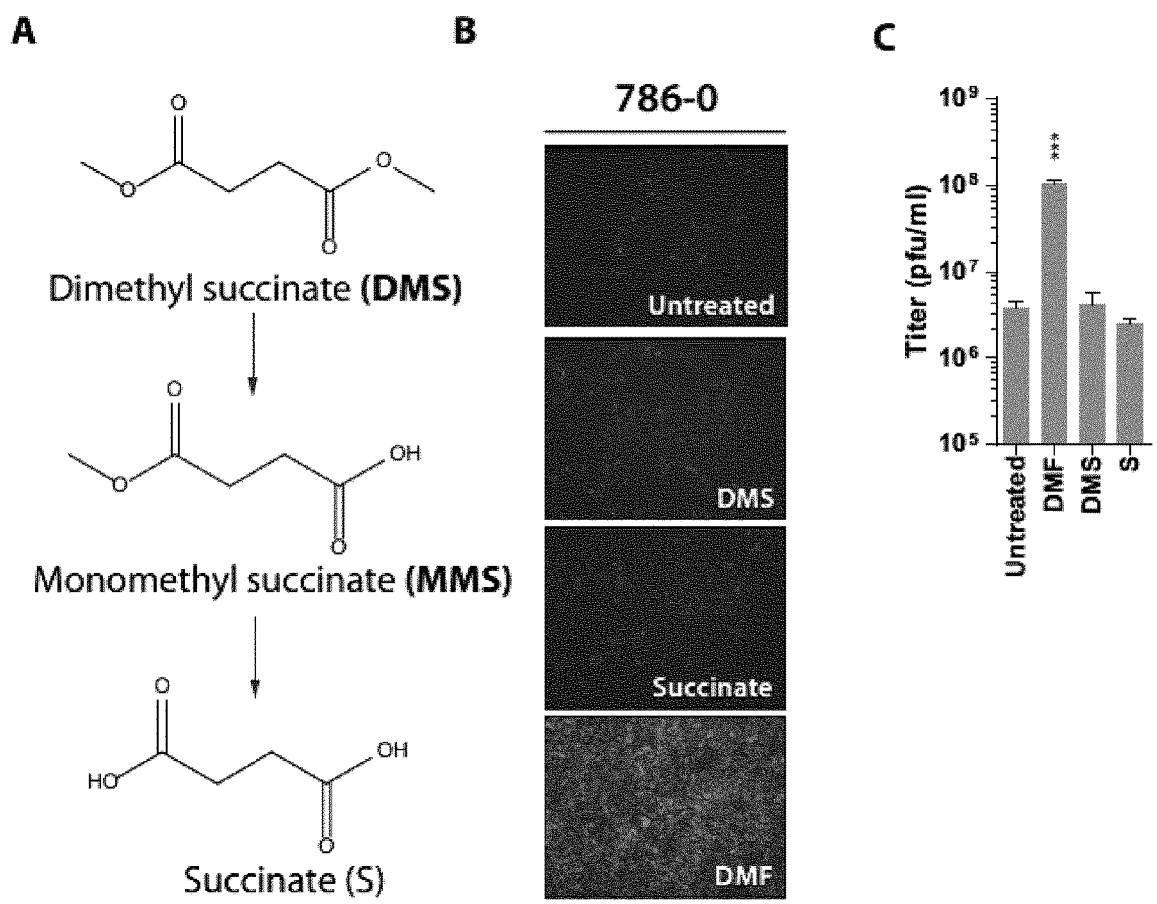
FIG. 6 shows that DMF inhibited NF-κB translocation upon infection. (A) Structure of DMS, MMS, S. (B-C) 786-0 were pretreated with indicated DMF analogues for 4 hours and subsequently infected with oncolytic VSVΔ51 expressing GFP at an MOI of 0.01. (B) 24 hours post infection fluorescent images were taken of the infected 786-0 cells. (C) Corresponding viral titers were determined 48 hours post infection from supernatants. (N=3; Error bars indicate SD; one-way ANOVA; * p<0.001, as compared to the untreated counterpart) (D) GSH levels were determined in 786-0 cells after a 4-hour treatment with FMAEs. (N=4; Error bars indicate SD; one-way ANOVA; * p<0.001, as compared to the untreated counterpart). (E) Heatmap showing the expression levels of the differentially expressed oxidative stress genes. Expression of genes was normalized to values obtained for untreated, infected control. (F) hmox1 expression levels quantified by qPCR from 786-0 cells after a 6-hour treatment with FMAEs. (N=3; Error bars indicate SD). (G) 786-0 were growth in presence of BSO (2 mM) for 7 days and pretreated with DMF (200 µM) for 4 hours and subsequently infected with oncolytic VSVΔ51 expressing GFP at an MOI of 0.01. Corresponding viral titer were determined 48 hours post infection from supernatants. (N=3; Error bars indicate SD). (H) siNRF2 knockdown 786-0 cells were treated with DMF and infected as in (G). Corresponding viral titers were determined 24 hours post infection from supernatants. RNA was extracted and expression of nrf2 and ifitm1 genes was quantified by qPCR (N=3; Error bars indicate SD). (I-J) Cytoplasmic and nuclear protein fraction were extracted from 786-0 cells treated with DMF (200 µM) for 4 hours and (I) subsequently infected with oncolytic VSVΔ51 expressing GFP at an MOI of 1 for 8 hours, or (J) treated with TNFα (30 ng/ml) for 30 min. Cell lysates were probed for multiple proteins as indicated, by western blot. (K) 786-0 were pretreated with NF-κB inhibitors (IKK16 [10 µM], TPCA1 [40 µM]) for 4 hours and subsequently co-treated with DMF (150 µM) and oncolytic VSVΔ51 expressing GFP at an MOI of 0.01. Corresponding viral titers were determined 24 hours post infection from supernatants. (N=3; Error bars indicate SD; one-way ANOVA; ***p<0.001, as compared to the untreated counterpart).
Figure 6:
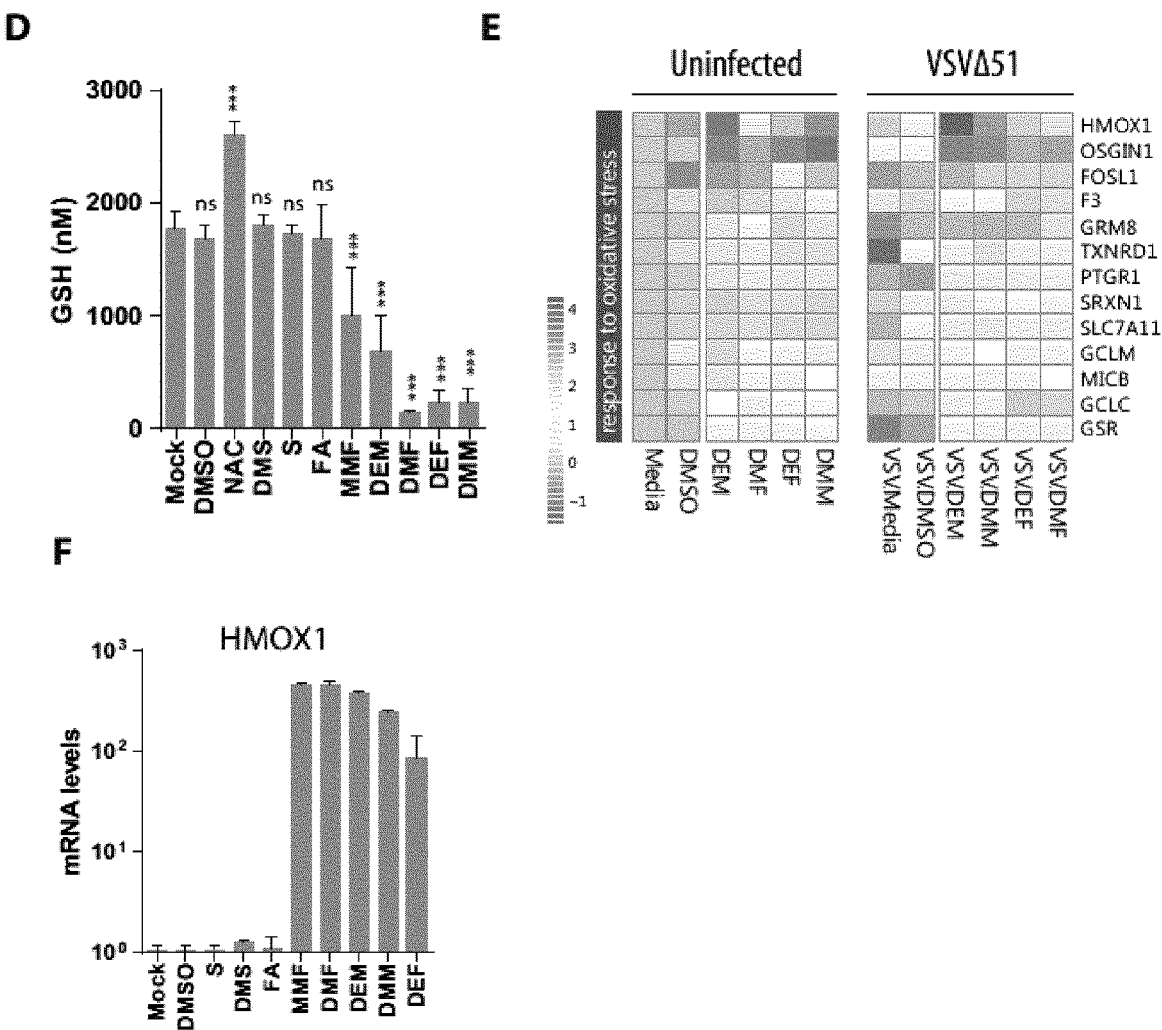
Figure 6:
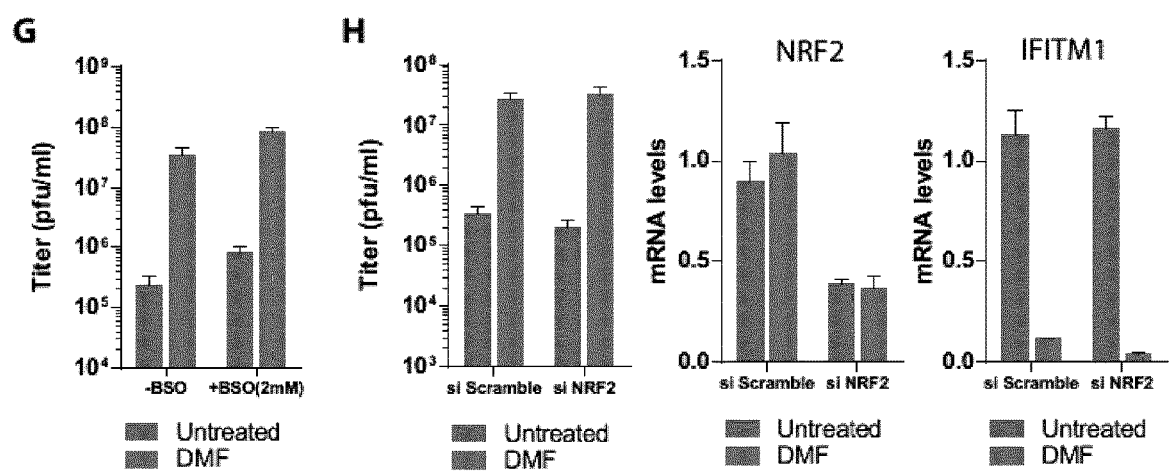
Figure 6:
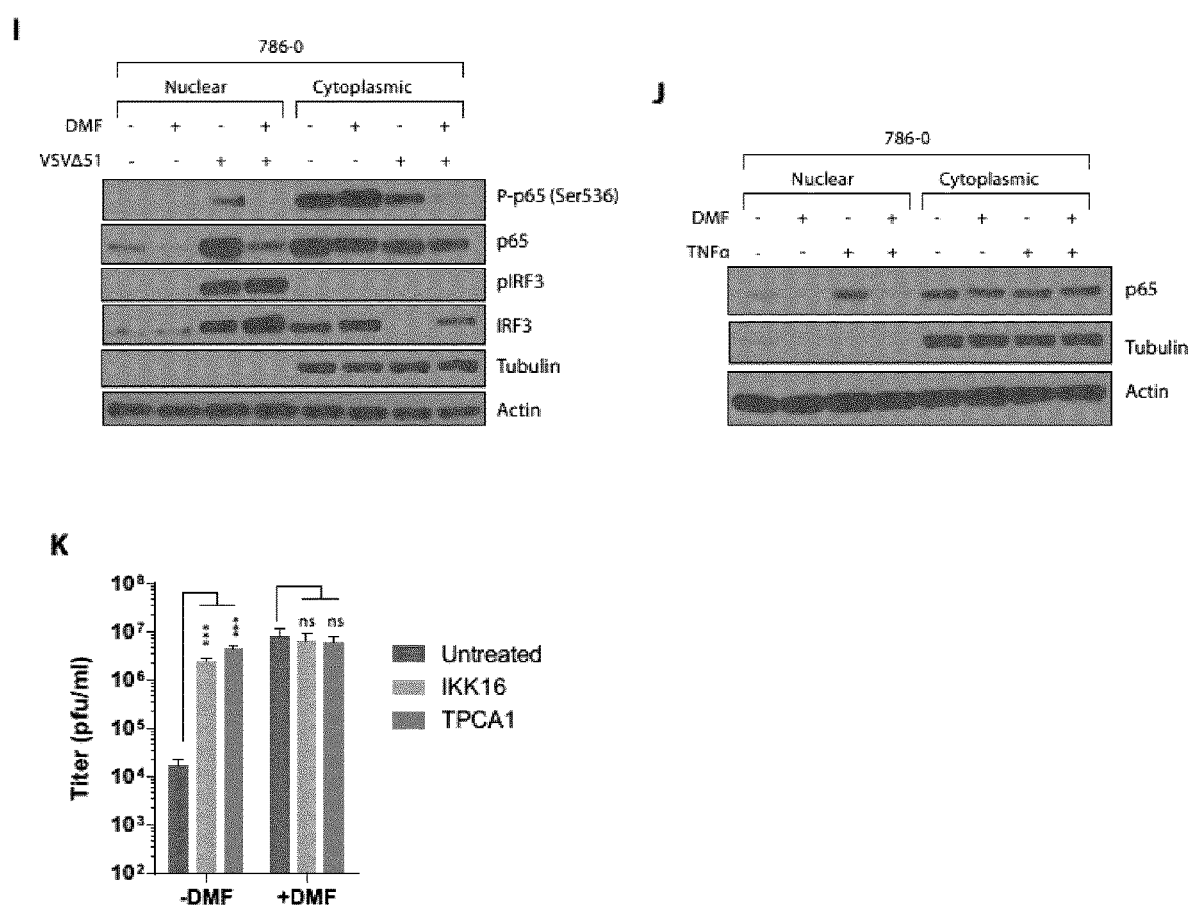

Example 6 Fumaric and Maleic Acid Esters Promote Infection Through NF-κB Inhibition Independently of GSH Depletion Our data clearly implicate an effect of multiple FMAEs on the antiviral response, and so we further investigated the molecular chain of events leading to these effects. DMF, DEM, DEF, and MMF share a common α,β-unsaturated carbon, which is attacked by GSH in a Michael addition reaction and which is implicated in the capacity of these compounds to deplete cellular GSH and activate the antioxidant response [40]. We therefore tested the impact of dimethyl succinate (DMS) (FIG. 6A), which lacks this functional moiety. We found that DMS had no impact on viral output (FIGS. 6, B and C), nor did the hydrolysed form of DMS, succinate (S). In contrast with FA, DMS, and S, all FMAEs were able to deplete GSH (FIG. 6D). However, the proviral activity of DMF was still evident following pre-depletion of cellular levels of GSH by culturing cells for 10 days in the presence of buthionine sulfoximine (BSO), an inhibitor of Glutamate Cysteine Ligase (GCL) required for the synthesis of GSH (FIG. 6G). In parallel with their impact on antiviral gene expression by microarray, FMAEs also induced robust expression of multiple genes involved in the antioxidant response (FIG. 6E). In particular, hmox1 expression as determined by real-time PCR was consistently up-regulated well over 100-fold by FMAEs (FIG. 6F), but not by treatment with FA, DMS, or S (FIG. 6F). DMF and other FMAEs have been shown to induce nuclear translocation of NRF2 via covalent modification of KEAP1, which leads to the induction of antioxidant genes [41]. This is consistent with our observation of the induction of hmox1 and other NRF2 target genes by FMAEs but not FA, DMS, or S (FIGS. 6 E and F). To determine whether the proviral effect of DMF is dependent on NRF2 activity, siRNA knockout against NRF2 was performed. We found that knockdown against NRF2 did not block the capacity of DMF to enhance VSVΔ51 infection, nor to inhibit antiviral factor ifitm1 (FIG. 6H). Furthermore, DMF was able enhance infection in a number of cell lines harboring KEAP1 mutations (A549 [42], CT26WT [43]) (FIG. 1D). Altogether these data suggest that the ability of FMAEs to enhance infection requires the α,β-unsaturated carbon involved in GSH depletion, but that GSH depletion, nor NRF2 activity is not likely a key mediator of this phenomenon. Given DMF was previously shown to inhibit cytokine production when stimulated with LPS via inhibition of NF-κB nuclear entry [44-45], we looked at nuclear and cytoplasmic fractionations of infected cells. Probing for NF-κB subunit p65 revealed that upon infection or TFNα stimulation, DMF inhibits phosphorylation and translocation of this transcription factor, involved in the transcription of IFNβ particularly but also in the response to type I IFN (FIG. 6I, J).

Example 7 MMF Increases Lentivirus Produced from 293-T Cells

Figure 7:
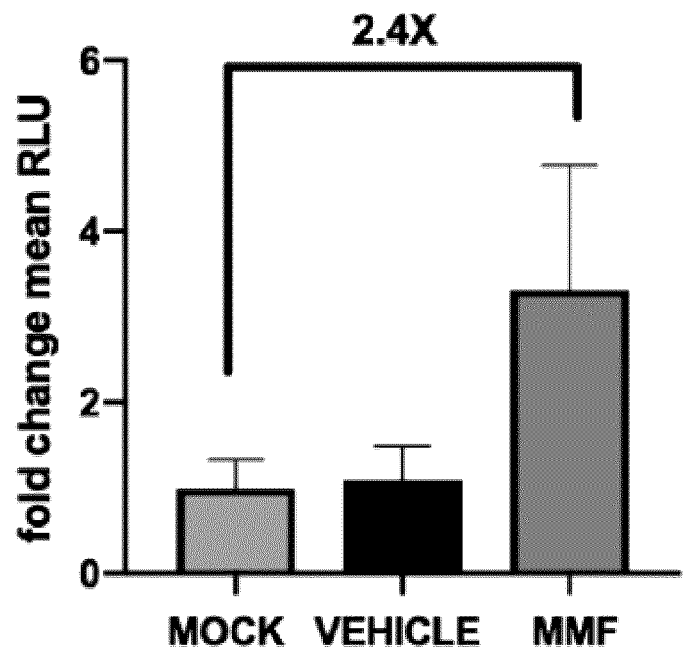
FIG. 7 shows that MMF increased lentivirus produced from 293-T cells. 293-T cells were seeded in 96-well plates using DMEM+10% FBS+35 mM HEPES and incubated at 37C 5% $CO_2$. Cells were treated with MMF, vehicle alone (DMSO), or mock treated with media, in triplicate wells and transfected with a 4-plasmid $3^{rd}$ generation lentivirus luciferase reporter gene system using PEIpro (Polyplus Transfection, France) then incubated at 37° C. in 5% $CO_2$ for 48 h. Following incubation, the supernatant was transferred to a new 96w plate, which was sealed with an adhesive plate sealer and immediately frozen at −80° C. To measure the amount of LV produced: HT1080 cells were seeded in 96w plates at 5e3 cells/well in 100 µl volume using DMEM+10% FBS+35 mM HEPES and incubate at 37° C. 5% $CO_2$ overnight. The next morning 80 µl of the growth media was removed and replaced with 30 µl thawed LV-containing supernatant, in duplicate. The plate was spun at 890G for 10 minutes then incubated at 37° C. 5% $CO_2$ for 6 h. The cells were then supplemented with 100 µl DMEM+10% FBS+35 mM HEPES and incubated at 37° C. 5% $CO_2$ for 72 h. Luciferase expression was measured using a Biotek plate reader following addition of luciferin to each well (2 mg/ml; 25 µl per well). Data represents the fold change of mean RLU calculated from six replicate wells per condition, versus mock treatment. The difference between mock and MMF condition was significant by ANOVA (p<0.0001).

FIG. 7 shows that MMF treatment of 293T cells that were transfected with a 4-plasmid 3rd generation replication incompetent lentivirus system, wherein the resulting lentivirus encodes luciferase, resulted in a 2.4 fold increase in virus yield compared to media or vehicle (DMSO) alone. The titer of virus was determined by luciferase expression following transfer of lentivirus-containing supernatants to permissive HT1080 cells. This indicates that MMF significantly increases the production of replication incompetent lentivirus made by co-transfection of plasmids in immortalized cells.

Example 8 DMF Increases Influenza Virus Titer in VeroSF Cells

FIG. 8 shows that DMF treatment of VeroSF cells, which are Vero cells adapted to grow in serum-free media, led to a 3.0-3.8X fold increase (compared to DMSO vehicle and Media alone respectively) of influenza A H1N1 FM/1/47 yield. In this example, virus nucleoprotein antigen was quantified by ELISA compared to a standard control and this data was used to estimate virus titer. These data directly indicate that DMF enhanced the production of influenza virus protein antigen, and indirectly that influenza virus yield was similarly improved.

Materials and Methods

Drugs, chemicals and cytokines. Drugs, chemicals, and cytokines and their respective supplier and solvent used in this study are bellow.

| Name | Abbreviation | Solvent | Supplier |
|---|---|---|---|
| Diethyl maleate | DEM | DMSO | Sigma-Aldrich |
| Diethyl fumarate | DEF | DMSO | Sigma-Aldrich |
| Dimethyl maleate | DMM | DMSO | Sigma-Aldrich |
| Diethyl fumarate | DMF | DMSO | Sigma-Aldrich |
| Monomethyl fumarate | MMF | Water | Sigma-Aldrich |
| Fumaric acid | FA | DMSO | Sigma-Aldrich |
| Dimethyl succinate | DMS | DMSO | Sigma-Aldrich |
| Sodium succinate dibasic hexahydrate | S | Water | Sigma-Aldrich |
| IKK16 | IKK16 | DMSO | Cayman Chemical |
| TPCA1 | TPCA1 | DMSO | Abcam |
| L-Glutathione, reduced | GSH | Water | Cayman Chemical |
| N-acetyl-L-cysteine | NAC | Water | Sigma-Aldrich |
| L-Buthionine-sulfoximine | BSO | Water | Sigma-Aldrich |
| D-Luciferin, potassium salt | Luciferin | PBS | Biotium |
| Human IFN 2a alpha | IFNα | PBS | Sigma-Aldrich |
| Human IFN beta | IFNβ | PBS | PBL |
| Human TNF alpha | TNFα | PBS | R&D Systems |

Cell lines. B16F10 (melanoma), CT26WT (colon), 76-9 (sarcoma), 293-T cells, EMT6 (breast), K7M2 (osteosarcoma) mouse cancer cell lines; Vero monkey kidney cells (and Vero cells adapted to serum free media); and 786-0 (colon), A549 (lung), HT29 (colon), M14 (melanoma), OVCA433 (ovary), SKOV3 (ovary), EKVX (lung), HT1080 (sarcoma) human cancer cells were cultured in HyQ high-glucose Dulbecco's modified Eagle's medium (DMEM) (Hyclone) or Roswell Park Memorial Institute (RPMI)-1640 medium (Corning) supplemented with 10% fetal calf serum (CanSera), penicillin/streptomycin (Gibco). All cell lines were incubated at 37° C. in a 5% $CO_2$ humidified incubator. All cells were tested to ensure they are free of *Mycoplasma* contamination.

Human-derived cell lines. Ovarian cancer primary cultures were derived from the ascites of individuals with ovarian cancer during routine paracentesis according to Ottawa Health Science Network Research Ethics Board (OHSN-REB) protocol number 20140075-01H. These cells were maintained in complete Dulbecco's Modified Eagle's medium supplemented with 10% fetal bovine serum. These cultures have been characterized and cryopreserved for use as experimental models. Melanoma primary cultures were derived from excised surgical specimens. The surgeries were performed at the Ottawa Hospital and specimens were taken following the receipt of patient consent according to the OHSN-REB #20120559-01. Primary cultures were maintained in Roswell Park Memorial Institute (RPMI)-1640 medium supplemented with 10% fetal bovine serum. Primary cultures were established following scalpel-mediated homogenization of tumor specimens and filtering the homogenate through a 70 μm nylon mesh cell strainer (ThermoFisher Scientific). Homogenate was maintained in culture with periodically-refreshed media until sufficient cellular proliferation occurred for experimental purposes. Both primary melanoma cultures have been characterized and cryopreserved for use as experimental models.

Viruses and quantification. Rhabodviruses. The Indiana serotype of VSV (VSVΔ51 or wild type) was used throughout this study and was propagated in Vero cells. VSVΔ51-expressing GFP or firefly luciferase are recombinant derivatives of VSVΔ51 described previously [30]. All viruses were propagated on Vero cells and purified on 5-50% Optiprep (Sigma, St Louis, MO) gradient and all virus titers were quantified by the standard plaque assay on Vero cells as previously described [46]. The number of infectious virus particles was expressed as plaque-forming unit (PFU) per milliliter (ml). Adenovirus. The Ad5-luciferase (adenovirus serotype 5 expressing firefly-luciferase) were used in these studies. Herpes simplex virus. The HSV-1 N212 expressing GFP. HSV virus titres were quantified by the standard plaque assay on Vero cells as previously described. Sindbis virus. The Sindbis virus was quantified by the standard plaque assay in Vero cells. Plaques were counted 3 days postinfection. Lentivirus. The Lentivirus with luciferase reporter gene system were quantified using a Biotek plate reader following the addition of luciferin to supernatants. Influenza. Influenza A/FM/1/47 viruses were used, and absorbance values were obtained by ELISA.

Cell viability assay. The metabolic activity of the cells was assessed using alamarBlue® (Bio-Rad) according to the manufacturer's protocol. Fluorescence was measured at 590 nm upon excitation at 530 nm using a Fluoroskan Ascent FL (Thermo Labsystems).

Microarray and analysis. 786-0 cells were plated at a density of $1\times10^6$ in 6-well dishes and allowed to adhere overnight. The next day, cells were pretreated for 4 hours with DEM (350 µM), DEF (350 µM), DMM (300 µM), DMF (200 µM) or the vehicle. Following pre-treatment, the cells were infected with VSVΔ51 at an MOI of 0.01 or mock-infected. 24 hours post-infection, RNA was collected using an RNA-easy kit (Qiagen). Biological triplicates were subsequently pooled and RNA quality was measured using Agilent 2100 Bioanalyzer (Agilent Technologies) before hybridization to Affymetrix Human PrimeView Array (The Centre for Applied Genomics, The Hospital for Sick Children, Toronto, Canada). Microarray data was processed using Transcriptome Analysis Console (TAC) 3.0 under default parameters of Gene Level Differential Expression Analysis. Fold change in gene expression was calculated for each gene in relation to uninfected, untreated control. Heatmaps of normalized expression values were generated using R package pheatmap. Volcano plots of gene expression values were generated using R. Gene ontology enrichment analysis was evaluated using GOrilla [47] following correction for multiple hypothesis testing (Benjamini-Hochberg). Raw and processed microarray data have been deposited in NCBI-Gene Expression Omnibus database (GSE97328).

Mouse tumor model. CT26WT model. Six-week-old female BALB/c mice obtained from Charles River Laboratories were given subcutaneous tumors by injecting $5\times10^5$ syngeneic CT26WT cells suspended in 100p PBS. 11 days post-implantation, tumors were treated intratumorally (i.t.) once with 200 mg/kg of DMF (dissolved in DMSO) or the vehicle alone. 4 hours later, tumors were intratumorally injected with $1\times10^8$ PFU (in 25 µl PBS) of VSVΔ51-expressing firefly luciferase. HT29 model. Six-week-old female BALB/c nude mice were given subcutaneous tumors by injecting $5\times10^6$ syngeneic HT29 cells suspended in 100 µl serum-free DMEM and 100 µl Geltrex (Thermo Fisher). When tumors grew to approximately 5 mm×5 mm (11 days post-implantation), mice were treated intratumorally once with 200 mg/kg of DMF (dissolved in DMSO) or the vehicle as indicated. Four hours later, tumors were injected intratumorally with $1\times10^8$ PFU of VSVΔ51-expressing firefly luciferase. B16F10 model. Six-week-old female C57BL/6 mice obtained from Charles River Laboratories were given subcutaneous tumors by injecting $5\times10^5$ syngeneic B16F10 cells suspended in 100 µl PBS. 11 days post-implantation, tumors were treated intratumorally (i.t.) once with 50 mg/kg of DMF (dissolved in DMSO) or the vehicle alone. 4 hours later, tumors were intratumorally injected with $1\times10^8$ PFU (in 25 µl PBS) of VSVΔ51-expressing firefly luciferase. Tumor sizes were measured every other day using an electronic caliper. Tumor volume was calculated as (length$^2$×width)/2. For survival studies, mice were culled when tumors had reached 1,500 mm$^3$. For in vivo imaging, an IVIS (Perkin Elmer) was used as described previously [36]. The bioluminescent signal intensities in each mouse were quantified using Living Image® v2.50.1 software. Sample size in all animal experiments was greater than n≥5. Mice were randomized to the different treatment groups according to tumor size in all experiments. Mice with no palpable tumors on initial treatment day were excluded from study. The investigators were not blinded to allocation during experiments and outcome assessment. All experiments were performed in accordance with the University of Ottawa Animal Care and Veterinary Services guidelines for animal care under the protocol OHRI-2265 and OHRI-2264.

Ex vivo mouse model. BALB/c mice were implanted with subcutaneous CT26WT. Mice were sacrificed after tumors had reached at least 10 mm×10 mm in size. Tumor, lung, spleen and brain tissue were extracted from the mice, cut into 2 mm thick slices and cored into 2 mm×2 mm pieces using a punch biopsy. Each tissue core was incubated in 1 mL of Dulbecco's Modified Eagle's Medium (DMEM) supplemented with 10% fetal bovine serum, 30 mM HEPES and were incubated at 37° C. in a 5% $CO_2$ humidified incubator. Cores were treated for 4 hours with indicated concentrations of chemical compounds. Subsequently the cores were then infected VSVΔ51-GFP. GFP pictures were taken for each core 24 hours post infection.

Ex vivo human samples. Tumor samples were acquired from consenting individuals during surgery and specimens were manipulated as previously depicted [48]. Approval was granted by the Ottawa Health Science Network Research Ethics Board for all studies requiring human tissue samples (OHSN-REB #2003109-01H and OHSN-REB #20120559-01). Patient provided their written, informed consent in accordance with Declaration of Helsinki guidelines.

Immunoblotting. Cells were pelleted and lysed on ice for 30 minutes using 50 mM HEPES, pH 7.4, 150 mM NaCl, 10 mM EDTA, 10 mM $Na_4P_2O_7$, 100 mM NaF, 2 mM $Na_3VO_4$, protease inhibitor cocktail (Roche) and 1% Triton X-100. For nuclear and cytoplasmic extracts the NE-PER™ Nuclear and Cytoplasmic Extraction kit (ThermoFisher Scientific, Rockford IL) was used according to the provided protocol. Following protein determination by Bradford assay (Bio-Rad Protein Assay Solution), 20 µg of clarified cell lysates were electrophoresed on NuPAGE® Novex® 4-12% Bis-Tris precast Gels (ThermoFisher Scientific) using the XCell SureLock® mini-cell System (ThermoFisher Scientific) and transferred on nitrocellulose membranes (Hybond-C, Bio-Rad). Blots were blocked with 5% BSA or milk and probed with antibodies specific for phospho-Stat1 (Tyr701, #9171, Cell Signalling Technology, used at 1:1000) and Stat1 (#9172, Cell Signalling Technology, used at 1:1000), Stat2 (#72604, Cell Signalling Technology, used at 1:1000), phospho-Stat2 (#884105, Cell Signalling Technology, used at 1:1000), IFITM1 (#60074-1-Ig, Proteintech Group, used at 1:1000, in 5% milk), VSV (a gift from Dr Earl Brown, used at 1:2000), HMOX1 (#70081, Cell Signalling Technology, used at 1:2000) or β-Actin (#4970, Cell Signalling Technology, used at 1:1000). Blots were then probed with a goat anti-rabbit or mouse peroxidase-conjugated antibodies (Jackson Immunoresearch Labs, West Grove, PA). Bands were visualized using the Supersignal West Pico Chemiluminescent substrate (ThermoFisher Scientific).

ELISA. 786-0 cells plated in 12-well dishes were pretreated with compound or the vehicle for 4 h, and subsequently infected with VSVΔ51-GFP at indicated MOI or left uninfected. Cell supernatants were collected at different times post infection as indicated. IFN alpha and IFN beta quantifications were performed using the Verikine Human IFN alpha or IFN beta ELISA kit (PBL Assay Science) as per the manufacturer's instructions. Absorbance values at 450 nM were measured on a Multiskan Ascent Microplate Reader (MXT Lab Systems).

Quantitative real-time PCR. 786-0 cells were treated for 6 h with indicated chemical compound or the vehicle. Cells were collected and RNA extraction was performed using the Qiagen RNeasy kit (Qiagen). RNA quantity and purity was assessed using a NanoDrop ND-1000 spectrophotometer (Thermo Scientific) RNA was converted to cDNA with RevertAid H Minus First Strand cDNA Synthesis Kit (Thermo Scientific). Real-time PCR reactions were performed according to the manufacturer's protocol with the QuantiTect SYBR Green PCR kit (Qiagen) on a 7500 Fast Real-Time PCR system (Applied Biosystems). Gene expression relative to GAPDH or b-actin. Fold induction was calculated relative to the untreated/uninfected samples for each gene. List of qPCR primers used:

```
gapdh (For-ACAGTCAGCCGCATCTTCTT  (SEQ ID NO: 1);

Rev-GTTAAAAGCAGCCCTGGTGA)  (SEQ ID NO: 2)

hmox1

(For-ACTGCGTTCCTGCTCAACAT  (SEQ ID NO: 3);

Rev-GGGGCAGAATCTTGCACTTT)  (SEQ ID NO: 4)

nrf2

(For-CAACTACTCCCAGGTTGCCC  (SEQ ID NO: 5);

Rev-AGTGACTGAAACGTAGCCGA)  (SEQ ID NO: 6)

ifitm1

(For-CCGTGAAGTCTAGGGACAGG  (SEQ ID NO: 7);

Rev-GGTAGACTGTCACAGAGCCG)  (SEQ ID NO: 8)
```

Supernatant transfer experiment. 786-0 cells plated in 12-well dishes were pretreated with FMAEs or the vehicle for 4 h, and subsequently infected with VSVΔ51AG-GFP at an MOI of 1. This virus can infect cells and replicate its genome but does not bud or spread further because of the lack of the viral G protein, thus preventing release of viral particles in the supernatant. 1 hour post-infection supernatant was removed, to remove residual drug and virus, and replenished with growth media supplemented with 10% fetal bovine serum. 12 or 16 hours post-infection supernatants were collected before being transferred to fresh 786-0 cells and process for further analysis.

siRNA. 786-0 cells, plated in 12-well dishes, were transfected with small interfering RNAs (100 nM) against NRF2 (ON-TARGETplus NFE2L2 siRNA #L-003755-00-0005, GE Dharmacon) or with a non-targeting scramble siRNA (GE Dharmacon).

Transfections were carried out according to manufacturer's protocol (Oligofectamine, Life Technologies).

Glutathione Assay. 786-0 cells plated in a 96-well plate were pretreated with FMAEs or the vehicle for 4 h, and the glutathione levels were determined using the GSH-Glo™ Glutathione Assay kit (Promega) as per the manufacturer's instructions. The luminescence-based assay is based on the conversion of a luciferin derivative into luciferin in the presence of glutathione, catalyzed by glutathione S-transferase (GST). The signal generated in a coupled reaction with firefly luciferase is proportional to the amount of glutathione present in the sample. The assay result is normalized using GSH standard solution provided with the kit. Luciferase expression was then measured on a SynergyMx Microplate Reader (BioTek).

Statistics. Statistical significance was calculated using Student's T-test with Welch's correction, one-way or two-way ANOVA test was performed as indicated in the figure legends. For all statistical analyses, differences were considered significant when a p-value was below or equal to 0.05. Error bars represent standard error of the mean. The Log-rank (Mantel-Cox) test was used to determine significant differences in plots for survival studies. Statistical analyses were performed using GraphPad Prism 6.0 and Microsoft Excel.

REFERENCES

[1] Arulanandam, R., et al., Microtubule disruption synergizes with oncolytic virotherapy by inhibiting interferon translation and potentiating bystander killing. Nat Commun, 2015. 6: p. 6410.

[2] Forbes, N. E., R. Krishnan, and J. S. Diallo, Pharmacological modulation of anti-tumor immunity induced by oncolytic viruses. Front Oncol, 2014. 4: p. 191.

[3] Liu, T. C. and D. Kim, Gene therapy progress and prospects cancer: oncolytic viruses. Gene Ther, 2008. 15(12): p. 877-84.

[4] Zamarin, D., et al., Localized oncolytic virotherapy overcomes systemic tumor resistance to immune checkpoint blockade immunotherapy. Sci Transl Med, 2014. 6(226): p. 226ra32.

[5] Russell, S. J., K. W. Peng, and J. C. Bell, Oncolytic virotherapy. Nat Biotechnol, 2012. 30(7): p. 658-70.

[6] Coffin, R. S., From virotherapy to oncolytic immunotherapy: where are we now? Curr Opin Virol, 2015. 13: p. 93-100.

[7] Lichty, B. D., et al., Going viral with cancer immunotherapy. Nat Rev Cancer, 2014. 14(8): p. 559-67.

[8] Zhang, J., et al., Maraba MG1 virus enhances natural killer cell function via conventional dendritic cells to reduce postoperative metastatic disease. Mol Ther, 2014. 22(7): p. 1320-32.

[9] Workenhe, S. T. and K. L. Mossman, Oncolytic virotherapy and immunogenic cancer cell death: sharpening the sword for improved cancer treatment strategies. Mol Ther, 2014. 22(2): p. 251-6.

[10] Andtbacka, R. H., et al., Talimogene Laherparepvec Improves Durable Response Rate in Patients With Advanced Melanoma. J Clin Oncol, 2015. 33(25): p. 2780-8.

[11] Lawler, S. E. and E. A. Chiocca, Oncolytic Virus-Mediated Immunotherapy: A Combinatorial Approach for Cancer Treatment. J Clin Oncol, 2015. 33(25): p. 2812-4.

[12] Hu, J. C., et al., A phase I study of OncoVEXGM-CSF, a second-generation oncolytic herpes simplex virus expressing granulocyte macrophage colony-stimulating factor. Clin Cancer Res, 2006. 12(22): p. 6737-47.

[13] Fumaric Acid Esters in the management of psoriasis, Balak, Psoriasis: Targets and Therapy, 2015, 5, 9-23

[14] L. Kappos, et al., BG-12 Phase IIb Study Investigators, Efficacy and safety of oral fumarate in patients with relapsing-remitting multiple sclerosis: a multi-centre, randomised, double-blind, placebo-controlled phase IIb study, Lancet 372, 1463-1472 (2008).

[15] R. A. Linker, D.-H. Lee, S. Ryan, A. M. van Dam, R. Conrad, P. Bista, W. Zeng, X. Hronowsky, A. Buko, S. Chollate, G. Ellrichmann, W. Bruck, K. Dawson, S. Goelz, S. Wiese, R. H. Scannevin, M. Lukashev, R. Gold, Fumaric acid esters exert neuroprotective effects in neuroinflammation via activation of the Nrf2 antioxidant pathway, Brain 134, 678-692 (2011).

[16a] R. Loewe, W. Holnthoner, M. Gröger, M. Pillinger, F. Gruber, D. Mechtcheriakova, E. Hofer, K. Wolff, P. Petzelbauer, Dimethylfumarate Inhibits TNF-Induced Nuclear Entry of NF-κB/p65 in Human Endothelial Cells, The Journal of Immunology 168, 4781-4787 (2002).

[17] P. Albrecht, et al., Effects of dimethyl fumarate on neuroprotection and immunomodulation, J. Neuroinflammation 9, 163 (2012)

[18] J. C. U. Lehmann, J. J. Listopad, C. U. Rentzsch, F. H. Igney, A. von Bonin, H. H. Hennekes, K. Asadullah, W.-D. F. Docke, Dimethylfumarate induces immunosuppression via glutathione depletion and subsequent induction of heme oxygenase 1, J. Invest. Dermatol. 127, 835-845 (2007).

[19] S. X. Lin, L. Lisi, C. Dello Russo, P. E. Polak, A. Sharp, G. Weinberg, S. Kalinin, D. L. Feinstein, The anti-inflammatory effects of dimethyl fumarate in astrocytes involve glutathione and haem oxygenase-1, ASN Neuro 3 (2011), doi:10.1042/AN20100033.

[20] C. B. Burness, E. D. Deeks, Dimethyl fumarate: a review of its use in patients with relapsing-remitting multiple sclerosis, CNS Drugs 28, 373-387 (2014).

[21] J. J. Hoefnagel, H. B. Thio, R. Willemze, Long-term safety aspects of systemic therapy with fumaric acid esters in severe psoriasis, British Journal of (2003) (available at http://onlinelibrary.wiley.com/doi/10.1046/j.1365-2133.2003.05433.x/full).

[22] A. Atwan, J. R. Ingram, R. Abbott, M. J. Kelson, T. Pickles, A. Bauer, V. Piguet, in Cochrane Database of Systematic Reviews, (2015).

[23] 8. X. Xie, Y. Zhao, C.-Y. Ma, X.-M. Xu, Y.-Q. Zhang, C.-G. Wang, J. Jin, X. Shen, J.-L. Gao, N. Li, Z.-J. Sun, D.-L. Dong, Dimethyl fumarate induces necroptosis in colon cancer cells through GSH depletion/ROS increase/MAPKs activation pathway, Br. J. Pharmacol. 172, 3929-3943 (2015).

[24] N. E. B. Saidu, G. Noé, O. Cerles, L. Cabel, N. Kavian-Tessler, S. Chouzenoux, M. Bahuaud, C. Chéreau, C. Nicco, K. Leroy, B. Borghese, F. Goldwasser, F. Batteux, J. Alexandre, Dimethyl Fumarate Controls the NRF2/DJ-1 Axis in Cancer Cells: Therapeutic Applications, Mol. Cancer Ther. 16, 529-539 (2017).

[25] R. Loewe, T. Valero, S. Kremling, B. Pratscher, R. Kunstfeld, H. Pehamberger, P. Petzelbauer, Dimethylfumarate impairs melanoma growth and metastasis, Cancer Res. 66, 11888-11896 (2006).

[26] T. Valero, S. Steele, K. Neumüller, A. Bracher, H. Niederleithner, H. Pehamberger, P. Petzelbauer, R. Loewe, Combination of dacarbazine and dimethylfumarate efficiently reduces melanoma lymph node metastasis, J. Invest. Dermatol. 130, 1087-1094 (2010).

[27] I. Kaluzki, I. Hrgovic, T. Hailemariam-Jahn, M. Doll, J. Kleemann, E. M. Valesky, S. Kippenberger, R. Kaufmann, N. Zoeller, M. Meissner, Dimethylfumarate inhibits melanoma cell proliferation via p21 and p53 induction and bcl-2 and cyclin B1 downregulation, Tumour Biol. 37, 13627-13635 (2016).

[28] I. Kastrati, M. I. Siklos, E. L. Calderon-Gierszal, L. El-Shennawy, G. Georgieva, E. N. Thayer, G. R. J. Thatcher, J. Frasor, Dimethyl Fumarate Inhibits the Nuclear Factor KB Pathway in Breast Cancer Cells by Covalent Modification of p65 Protein, J. Biol. Chem. 291, 3639-3647 (2016).

[29] B. Gu, L. M. DeAngelis, Enhanced cytotoxicity of bioreductive antitumor agents with dimethyl fumarate in human glioblastoma cells, Anticancer Drugs 16, 167-174 (2005).

[30] D. F. Stojdl, B. D. Lichty, B. R. tenOever, J. M. Paterson, A. T. Power, S. Knowles, R. Marius, J. Reynard, L. Poliquin, H. Atkins, E. G. Brown, R. K. Durbin, J. E. Durbin, J. Hiscott, J. C. Bell, VSV strains with defects in their ability to shutdown innate immunity are potent systemic anti-cancer agents, Cancer Cell 4, 263-275 (2003).

[31] F. Le Boeuf, M. Selman, H. Hee Son, A. Bergeron, A. Chen, J. Tsang, D. Butterwick, R. Arulanandam, N. E. Forbes, F. Tzelepis, J. C. Bell, J. Werier, H. Abdelbary, J.-S. Diallo, Oncolytic Maraba virus MG1 as a treatment for Sarcoma, Int. J. Cancer (2017), doi: 10.1002/ijc.30813.

[32] C. Sheridan, Gene therapy finds its niche, Nat. Biotechnol. 29, 121-128 (2011).

[33] D. Moharregh-Khiabani, R. A. Linker, R. Gold, M. Stangel, Fumaric Acid and its esters: an emerging treatment for multiple sclerosis, Curr. Neuropharmacol. 7, 60-64 (2009).

[34] R. Bomprezzi, Dimethyl fumarate in the treatment of relapsing-remitting multiple sclerosis: an overview, Ther. Adv. Neurol. Disord. (2015), doi:10.1177/1756285614564152.

[35] C. G. Lemay, J. L. Rintoul, A. Kus, J. M. Paterson, V. Garcia, T. J. Falls, L. Ferreira, B. W. Bridle, D. P. Conrad, V. A. Tang, J.-S. Diallo, R. Arulanandam, F. Le Boeuf, K. Garson, B. C. Vanderhyden, D. F. Stojdl, B. D. Lichty, H. L. Atkins, K. A. Parato, J. C. Bell, R. C. Auer, Harnessing oncolytic virus-mediated antitumor immunity in an infected cell vaccine, Mol. Ther. 20, 1791-1799 (2012).

[36] M. H. Dornan, R. Krishnan, A. M. Macklin, M. Selman, N. El Sayes, H. H. Son, C. Davis, A. Chen, K. Keillor, P. J. Le, C. Moi, P. Ou, C. Pardin, C. R. Canez, F. Le Boeuf, J. C. Bell, J. C. Smith, J.-S. Diallo, C. N. Boddy, First-in-class small molecule potentiators of cancer virotherapy, Sci. Rep. 6, 26786 (2016).

[37] M.-C. Bourgeois-Daigneault, D. G. Roy, T. Falls, K. Twumasi-Boateng, L. E. St-Germain, M. Marguerie, V. Garcia, M. Selman, V. A. Jennings, J. Pettigrew, S. Amos, J.-S. Diallo, B. Nelson, J. C. Bell, Oncolytic vesicular stomatitis virus expressing interferon-6 has enhanced therapeutic activity, Molecular Therapy—Oncolytics 3, 16001 (2016).

[38] M. Selman, C. Rousso, A. Bergeron, H. H. Son, R. Krishnan, N. A. El-Sayes, O. Varette, A. Chen, F. Le Boeuf, F. Tzelepis, J. C. Bell, D. Crans, J.-S. Diallo, Multi-Modal Potentiation of Oncolytic Virotherapy by Vanadium Compounds, Mol. Ther. 0 (2017), doi: 10.1016/j.ymthe.2017.10.014.

[39] C. S. Robison, M. A. Whitt, The membrane-proximal stem region of vesicular stomatitis virus G protein confers efficient virus assembly, J. Virol. 74, 2239-2246 (2000).

[40] L. B. Sullivan, E. Martinez-Garcia, H. Nguyen, A. R. Mullen, E. Dufour, S. Sudarshan, J. D. Licht, R. J. Deberardinis, N. S. Chandel, The proto-oncometabolite fumarate binds glutathione to amplify ROS-dependent signaling, Mol. Cell 51, 236-248 (2013).

[41] M. S. Brennan, M. F. Matos, B. Li, X. Hronowski, B. Gao, P. Juhasz, K. J. Rhodes, R. H. Scannevin, Dimethyl Fumarate and Monoethyl Fumarate Exhibit Differential Effects on KEAP1, NRF2 Activation, and Glutathione Depletion In Vitro, PLoS One 10, e0120254 (2015).

[42] B. E. Hast, E. W. Cloer, D. Goldfarb, H. Li, P. F. Siesser, F. Yan, V. Walter, N. Zheng, D. N. Hayes, M. B. Major, Cancer-derived mutations in KEAP1 impair NRF2 degradation but not ubiquitination, Cancer Res. 74, 808-817 (2014).

[43] J. C. Castle, M. Loewer, S. Boegel, J. de Graaf, C. Bender, A. D. Tadmor, V. Boisguerin, T. Bukur, P. Sorn, C. Paret, M. Diken, S. Kreiter, Ö. Türeci, U. Sahin, Immunomic, genomic and transcriptomic characterization of CT26 colorectal carcinoma, BMC Genomics 15, 190 (2014).

[44] V. A. McGuire, T. Ruiz-Zorrilla Diez, C. H. Emmerich, S. Strickson, M. S. Ritorto, R. V. Sutavani, A. Weiβ, K. F. Houslay, A. Knebel, P. J. Meakin, I. R. Phair, M. L. J. Ashford, M. Trost, J. S. C. Arthur, Dimethyl fumarate blocks pro-inflammatory cytokine production via inhibition of TLR induced M1 and K63 ubiquitin chain formation, Sci. Rep. 6, 31159 (2016).

[45] H. Peng, M. Guerau-de-Arellano, V. B. Mehta, Y. Yang, D. J. Huss, T. L. Papenfuss, A. E. Lovett-Racke, M. K. Racke, Dimethyl fumarate inhibits dendritic cell maturation via nuclear factor κB (NF-κB) and extracellular signal-regulated kinase 1 and 2 (ERK1/2) and mitogen stress-activated kinase 1 (MSK1) signaling, J. Biol. Chem. 287, 28017-28026 (2012).

[46] J.-S. Diallo, M. Vähä-Koskela, F. Le Boeuf, J. Bell, Propagation, purification, and in vivo testing of oncolytic vesicular stomatitis virus strains, Methods Mol. Biol. 797, 127-140 (2012).

[47] E. Eden, R. Navon, I. Steinfeld, D. Lipson, Z. Yakhini, GOrilla: a tool for discovery and visualization of enriched GO terms in ranked gene lists, BMC Bioinformatics 10, 48 (2009).

[48] J.-S. Diallo, D. Roy, H. Abdelbary, N. De Silva, J. C. Bell, Ex vivo infection of live tissue with oncolytic viruses, J. Vis. Exp. (2011), doi:10.3791/2854.

All references cited herein and elsewhere in the specification are hereby incorporated by reference in their entireties.

What is claimed is:

1. A method of enhancing production, infection, growth, spread, or titer of an interferon-sensitive virus in an immortalized cell, a cancer cell or a tumor cell, the method comprising:
administering a compound of Formula (I), or a pharmaceutically acceptable salt or solvate thereof,

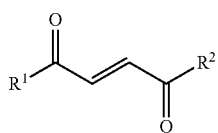

(I)

wherein $R^1$ and $R^2$ are each independently OH, $(C_{1-2})$ alkoxy or linear, branched or cyclic, saturated or unsaturated $(C_{3-20})$alkoxy; said alkoxy is optionally substituted with one or more halogen, OH, $(C_{1-4})$ alkyl, nitro or cyano;
wherein when one of $R^1$ and $R^2$ is OH, the other of $R^1$ and $R^2$ is not OH,
to the immortalized, cancer or tumor cell before, concurrently with, or after infection of the immortalized, cancer or tumor cell with the interferon-sensitive virus.

2. The method according to claim 1, wherein the interferon-sensitive virus is a non-interferon-sensitive virus genetically rendered interferon-sensitive, an attenuated interferon-sensitive virus, an interferon-sensitive oncolytic virus, or a non-replicating interferon-sensitive virus.

3. The method according to claim 2, wherein an oncolytic activity, a cell death activity, and/or cytotoxic activity of the interferon-sensitive oncolytic virus in the cancer cell or the tumor cell is enhanced or increased.

4. The method according to claim 2, wherein an immunotherapeutic activity of the interferon-sensitive oncolytic virus in the cancer cell or the tumor cell is enhanced, increased or potentiated.

5. The method according to claim 1, wherein the compound of Formula (I) is or comprises the structure of: Dimethylfumarate (DMF), diethylfumarate (DEF), monoethyl fumarate, or monomethyl fumarate (MMF), or a pharmaceutically acceptable salt or solvate thereof.

6. The method according to claim 1, wherein the interferon-sensitive virus is a reovirus, newcastle disease virus, polio virus, mumps virus, measles virus, influenza virus, Maraba virus, MG-1, Rabies virus, Rotavirus, Hepatitis A virus, Rubella virus, Dengue virus, Chikungunya virus, Respiratory Syncytial Virus, LCMV, lentivirus, replicating retrovirus, adenovirus, herpes simplex virus or rhabdovirus, or a variant or derivative thereof.

7. The method according to claim 2, wherein the interferon-sensitive oncolytic virus comprises a rhabdovirus which is vesicular stomatitis virus or a derivative or variant thereof.

8. The method according to claim 1, wherein the interferon-sensitive virus comprises a virus selected under specific growth conditions, subjected to one or more selection pressures, genetically modified using a recombinant technique, or any combination thereof.

9. The method according to claim 1, wherein the cell is mammalian.

10. The method according to claim 9, wherein the cell is human.

11. The method according to claim 1, wherein the immortalized cell, the cancer cell or the tumor cell comprises, Vero cells, HEK-293 cells, EB-66 cells, EB-bX cells, PER-.C6 cells, AGE1.CR cells, Age1.CS cells, Age1.HN cells, Age LRO cells, QOR2/2E11 cells, UMNSAH-DF1 cells, CHO cells, hybridoma cells, sf9 cells, R4 cells, 293-T cells, BHK21 cells, or MDCK cells, or cells from lymphoblastic leukemia, myeloid leukemia, adrenocortical carcinoma, AIDS-related cancer, AIDS-related lymphoma, anal cancer, appendix cancer, astrocytoma, atypical teratoid/rhabdoid tumor, basal cell carcinoma, bile duct cancer, bladder cancer, bone cancer, brain stem glioma, brain tumor, cerebellar astrocytoma, cerebral astrocytoma/malignant glioma, craniopharyngioma, ependymoblastoma, medulloblastoma, pineal parenchymal tumors of intermediate differentiation, supratentorial primitive neuroectodermal tumors and pineoblastoma, visual pathway and hypothalamic glioma, spinal cord tumors, breast cancer, bronchial tumors, Burkitt lymphoma, carcinoid tumor, central nervous system lymphoma, cervical cancer, chordoma, chronic lymphocytic leukemia, chronic myelogenous leukemia, chronic myeloproliferative disorders, colon cancer, cutaneous T-Cell lymphoma, embryonal tumors, endometrial cancer, ependymoma, esophageal cancer, extracranial germ cell tumor, extragonadal germ cell tumor, extrahepatic bile duct cancer, eye cancer, intraocular melanoma, retinoblastoma, gallbladder cancer, gastric (stomach) cancer, gastrointestinal carcinoid tumor, gastrointestinal stromal tumor (GIST), gestational trophoblastic tumor, glioma, hairy cell leukemia, head and neck cancer, hepatocellular (Liver) cancer, histiocytosis, Langerhans cell cancer, hypopharyngeal cancer, islet cell tumors, Kaposi sarcoma, laryngeal cancer, hairy cell leukemia, lip and oral cavity cancer, non-small cell lung cancer, small cell lung cancer, Hodgkin lymphoma, non-Hodgkin lymphoma, malignant fibrous histiocytoma of bone and osteosarcoma, medulloepithelioma, melanoma, mesothelioma, mouth cancer, multiple endocrine neoplasia syndrome, multiple myeloma/plasma cell neoplasm, nasal cavity and paranasal sinus cancer, nasopharyngeal cancer, neuroblastoma, oropharyngeal cancer, ovarian cancer, pancreatic cancer, parathyroid cancer, penile cancer, pharyngeal cancer, pheochromocytoma, pineal parenchymal tumors, pituitary tumor, pleuropulmonary blastoma, prostate cancer, rectal cancer, renal cell (kidney) cancer, renal pelvis and ureter cancer, transitional cell cancer, respiratory tract carcinoma, retinoblastoma, rhabdomyosarcoma, salivary gland cancer, uterine sarcoma, skin cancer, Merkel cell skin carcinoma, small intestine cancer, soft tissue sarcoma, squamous cell carcinoma, squamous neck cancer, testicular cancer, throat cancer, thymoma and thymic carcinoma, thyroid cancer, trophoblastic tumor, urethral cancer, uterine cancer, uterine sarcoma, vaginal cancer, vulvar cancer, or Wilms tumor.

12. A method for treating a tumor or cancer in a subject in need thereof, which comprises administering a compound of Formula (I), or a pharmaceutically acceptable salt or solvate thereof,

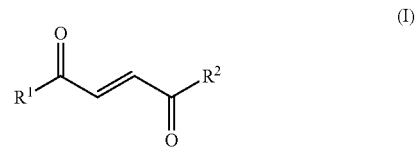

(I)

wherein $R^1$ and $R^2$ are each independently OH, $(C_{1-2})$ alkoxy or linear, branched or cyclic, saturated or unsaturated $(C_{3-20})$alkoxy; said alkoxy is optionally substituted with one or more halogen, OH, $(C_{1-4})$ alkyl, nitro or cyano;

wherein when one of $R^1$ and $R^2$ is OH, the other of $R^1$ and $R^2$ is not OH, to the subject before, after, or concurrently with administering an interferon-sensitive oncolytic virus to the subject.

13. The method according to claim 1, wherein the interferon-sensitive virus is a virus used to prepare a cancer vaccine, wherein the virus is a component of the vaccine, or the vaccine comprises the cell infected with the virus.

14. The method according to claim 1, wherein the interferon-sensitive virus is a virus used as a cancer gene therapy vector.

15. The method according to claim 2, wherein an immunotherapeutic activity of the interferon-sensitive oncolytic virus in the cancer cell or the tumor cell is enhanced, increased or potentiated for up-regulation of virus encoded transgenes and/or cytokines.

16. The method of claim 1, wherein the production, infection, growth, spread, or titer of the interferon-sensitive virus is potentiated as compared to the production, infection, growth, spread, or titer of the interferon-sensitive virus in the absence of the compound of Formula (I) or pharmaceutically acceptable salt or solvate thereof.

17. The method of claim 1, wherein the compound of Formula (I) is a compound represented by Formula (III) or a pharmaceutically acceptable salt or solvate thereof,

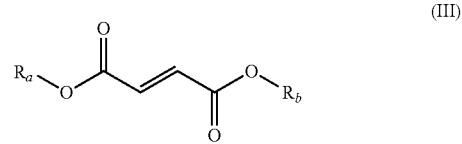

(III)

wherein $R_a$ and $R_b$ are the same or different and are each independently selected from hydrogen and $C_{1-10}$ alkyl, optionally substituted with one or more halogen, OH, $(C_{1-4})$ alkyl, nitro or cyano, and at least one of $R_a$ or $R_b$ is $C_{1-10}$ alkyl, optionally substituted with one or more halogen, OH, $(C_{1-4})$ alkyl, nitro or cyano.

18. The method of claim 12, wherein the compound of Formula (I) or pharmaceutically acceptable salt or solvate thereof enhances or increases virally induced cancer cell death.

* * * * *